(12) United States Patent
Nam et al.

(10) Patent No.: US 7,517,650 B2
(45) Date of Patent: Apr. 14, 2009

(54) METHOD OF DIAGNOSING BREAST CANCER AND COMPOSITIONS THEREFOR

(75) Inventors: Yun-sun Nam, Seongnam-si (KR); Seung-Hak Choi, Seongnam-si (KR); Jae-Heup Kim, Hwaseong-si (KR); Jung-joo Hwang, Suwon-si (KR); Yeon-Su Lee, Goyang-si (KR); Tae-jin Ahn, Seoul (KR)

(73) Assignee: Samsung Electronics Co., Ltd. (KR)

( * ) Notice: Subject to any disclaimer, the term of this patent is extended or adjusted under 35 U.S.C. 154(b) by 50 days.

(21) Appl. No.: 11/368,141

(22) Filed: Mar. 3, 2006

(65) Prior Publication Data

US 2006/0211023 A1    Sep. 21, 2006

(30) Foreign Application Priority Data

Mar. 5, 2005    (KR) ...................... 10-2005-0018439

(51) Int. Cl.
*C07H 21/04*  (2006.01)
*C12Q 1/68*   (2006.01)

(52) U.S. Cl. .................. 435/6; 435/91.1; 435/91.2; 536/23.1; 536/24.3

(58) Field of Classification Search ........................ None
See application file for complete search history.

(56) References Cited

U.S. PATENT DOCUMENTS

2003/0092019 A1*  5/2003  Meyer et al. ................... 435/6

FOREIGN PATENT DOCUMENTS

WO    9605306    2/1996

OTHER PUBLICATIONS

Friedman et al. (Am. J. Hum. Genet. vol. 60, pp. 313-319, 1997).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Fisher, R. A. "The Logic of Inductive Inference," Journal of the Royal Statistical Society Series A (1935) 98: 39-54.
Guatelli, J.C. et al. "Isothermal, In Virtro Amplification of Nucleic Acids by a Multienzyme Reaction Modeled After Retroviral Replication," Proc. Natl. Acad. Sci. USA (1990) 87: 1874-1878; Proc. Natl. Acad. Sci USA (1990) 87: 7797.
Kadouri, L. et al. "A Single-Nucleotide Polymorphism in the RAD51 Gene Modifies Breast Cancer Risk on BRCA2 Carriers, But Not in BRCA1 Carriers or Noncarriers," British Journal of Cancer (2004) 90: 2002-2005.
Kwoh, D.Y. et al. "Transription-Based Amplification System and Detection of Amplified Human Immunodeficiency Virus Type 1 with a Bead-Based Sandwich Hybridization Format," Proc. Natl. Acad. Sci. USA (1989) 86: 1173-177.
Landegren, R.K. et al. "A Ligase-Mediated Gene Detection Technique," Science (1988) 241: 1077-1080.
Mimori, K. et al. "A Single-Nucleotide Polymorphism of SMARCBI in Human Breast Cancers," Genomics (2002) 80(3): 254-258.
Ren, Z. et al. "Genetic Polymorphisms in the Human Growth Hormone-1 Gene (GH1) and the Risk of Breast Carconoma," Cancer (2004) 101(2):251-257.
Tower, G. B. et al. "The 2G Single Nucleotide Polymorphism (SNP) in the MMP-1 Promoter Contributes to High Levels of MMP-1 Transcription in MCF-7/ADR Breast Cancer Cells," Breast Cancer Research and Treatment (2003) 82: 75-82.
Wu, D.Y. and Wallace, R.B. "The Ligation Amplification Reaction (LAR)- Amplification of Specific DNA Sequences Using Sequential Rounds of Template-Dependent Ligation," Genomics ( 1989) 4: 560-569.
International Search Report for PCT/KR2006/000762. mailed Jun. 14, 2006.
Written Opinion for PCT/KR2006/000762. mailed Jun. 14, 2006.

* cited by examiner

*Primary Examiner*—Jeanine A Goldberg
(74) *Attorney, Agent, or Firm*—Cantor Colburn LLP

(57) ABSTRACT

A method of diagnosing breast cancer in an individual aged younger than 41 or older than 54 is provided. The method comprises obtaining a nucleic acid from the individual and determining a nucleotide at a polymorphic site of the nucleic acid. Polynucleotides specific to breast cancer, a microarray comprising the polynucleotides, and diagnostic kits are also provided.

2 Claims, 1 Drawing Sheet

METHOD OF DIAGNOSING BREAST CANCER AND COMPOSITIONS THEREFOR

CROSS-REFERENCE TO RELATED PATENT APPLICATION

This application claims priority from Korean Patent Application No. 10-2005-0018439, filed on Mar. 5, 2005, in the Korean Intellectual Property Office, the disclosure of which is incorporated herein in its entirety by reference.

1. Field of the Invention

The present invention relates to a method of diagnosing breast cancer using a polymorphic sequence specific to breast cancer, a polynucleotide specific to breast cancer, and a microarray and a diagnostic kit including the polynucleotide.

2. Description of the Related Art

The genomes of all organisms undergo spontaneous mutation in the course of their continuing evolution, generating variant forms of progenitor nucleic acid sequences. The variant forms of progenitor nucleic acid sequences may confer an evolutionary advantage or disadvantage, or may be neutral relative to the progenitor form. In some instances, a variant form confers a lethal disadvantage and is not transmitted to subsequent generations of the organism. In other instances, a variant form confers an evolutionary advantage to the species and is eventually incorporated into the DNA of most members of the species and effectively becomes the progenitor form. In many instances, both progenitor and variant form(s) survive and co-exist in a species population. The differences in a DNA sequence that coexist in a population are referred to as a polymorphism. Examples of polymorphisms include restriction fragment length polymorphism (RFLP), short tandem repeat (STR), and single-nucleotide polymorphism (SNP). The position in a DNA sequence at which such a sequence difference is found is referred to as a polymorphic site.

A SNP is a polymorphism in which a single nucleotide varies in a DNA sequence. When a SNP occurs in a protein coding sequence within a gene, one of the polymorphic forms may give rise to a non-synonymous codon change causing expression of a variant protein that may have altered properties. When a SNP occurs in non-coding sequences of a gene, one of the polymorphic forms may also cause expression of a variant protein, for example, as a result of defective splicing of mRNA. However, many SNPs have no apparent phenotypic effects.

It is known that human SNPs occur at a frequency of about 1 per 1,000 base pair (bp). When such a SNP induces a phenotypic effect such as the presence or absence of a disease, polynucleotides containing an allele of the SNP can be used as primers or probes for diagnosis of the disease. Monoclonal antibodies specifically binding with an allele of the SNP can also be used in the diagnosis of a disease. Currently, research into the nucleotide sequences and functions of SNPs is being performed by many research institutes. The nucleotide sequences and other experimental results on identified SNPs have been put in databases to be easily accessible. Even though findings available to date show that specific SNPs exist in various genes or cDNAs of the human genome, the phenotypic effects of most human SNPs have not yet been discovered.

Currently, breast cancer is diagnosed by X-ray, ultrasonic diagnosis, or biochemical or molecular biological techniques. Among these techniques, molecular biological techniques cannot provide early diagnosis of breast cancer. Approximately 3 to 30 SNP sites associated with breast cancer have been identified in BRCA1 and BRCA2 genes by Myriad Genetics, Inc. SNP markers associated with breast cancer are individually used in currently available diagnostic methods for the detection of breast cancer. However, there are no reports of a relationship between breast cancer and multilocus markers, which are combinations of individual SNP markers, or a method of diagnosing breast cancer using the multilocus markers.

SUMMARY OF THE INVENTION

The present invention provides a method of diagnosing breast cancer in an individual aged younger than 41 or older than 54 using a breast cancer-specific polymorphic sequence.

The present invention also provides a breast cancer-specific polynucleotide for an individual aged younger than 41 or older than 54.

The present invention also provides a microarray and a diagnostic kit comprising a breast cancer-specific polynucleotide.

BRIEF DESCRIPTION OF THE DRAWING

The above and other features and advantages of the present invention will become more apparent by describing in detail exemplary embodiments thereof with reference to the attached drawing in which.

DETAILED DESCRIPTION OF THE INVENTION

Figure 1:
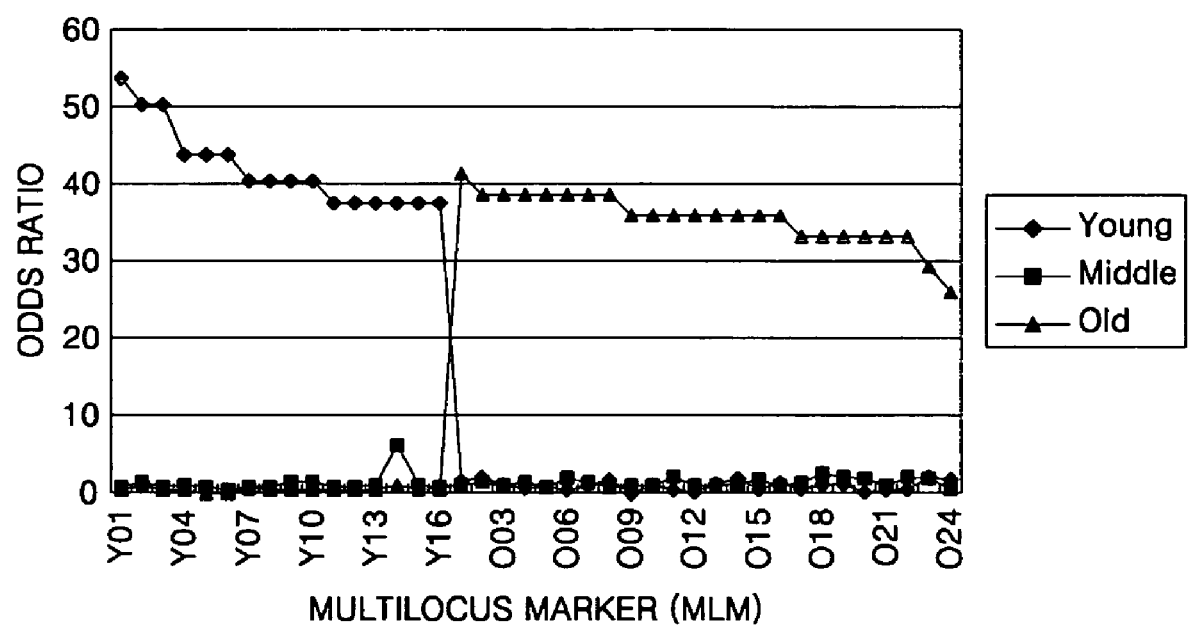
FIG. 1 is a graph illustrating an odds ratio with respect to a multilocus marker in each of young, middle, and old age groups.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

The present invention provides a method of diagnosing breast cancer in an individual aged younger than 41, which includes isolating a nucleic acid from the individual and determining a nucleotide of a polymorphic site of the nucleic acid. Determining the nucleotide of the polymorphic site can comprise determining a genotype of a polymorphic site (position 101) of at least one polymorphic sequence selected from polymorphic sequences in Table 1 below.

TABLE 1

| ID | rs | SEQ ID NO | A1 | A2 |
|---|---|---|---|---|
| SMBC_003 | rs1020445 | 2 | G | A |
| SMBC_006 | rs355510 | 4 | G | A |
| SMBC_008 | rs1477454 | 5 | G | A |
| SMBC_009 | rs422679 | 6 | C | T |
| SMBC_013 | rs916380 | 9 | T | C |
| SMBC_014 | rs6791 | 10 | A | G |
| SMBC_018 | rs729662 | 12 | A | G |
| SMBC_020 | rs1381067 | 13 | T | C |
| SMBC_022 | rs6668 | 14 | T | C |
| SMBC_025 | rs3824414 | 15 | T | C |
| SMBC_031 | rs198550 | 17 | G | A |
| SMBC_034 | rs476476 | 18 | C | T |
| SMBC_035 | rs10699 | 19 | G | A |
| SMBC_037 | rs736869 | 20 | T | C |
| SMBC_042 | rs2303114 | 21 | T | C |
| SMBC_046 | rs2347597 | 22 | T | C |
| SMBC_048 | rs5277 | 23 | C | G |
| SMBC_054 | rs2077647 | 24 | C | T |
| SMBC_056 | rs3218625 | 25 | C | T |
| SMBC_060 | rs2228480 | 26 | G | A |
| SMBC_061 | rs1372425 | 27 | C | T |
| SMBC_062 | rs841229 | 28 | G | A |
| SMBC_064 | rs355499 | 29 | C | T |
| SMBC_068 | rs1801132 | 30 | C | G |
| SMBC_071 | rs2518723 | 31 | T | C |
| SMBC_072 | rs12628 | 32 | T | C |
| SMBC_076 | rs2279901 | 33 | A | G |
| SMBC_087 | rs3731239 | 36 | C | T |

In Table 1, the column labeled ID presents the name of a polymorphic sequence comprising a SNP (also referred to herein as a SNP marker). Herein, the term "polymorphic sequence" refers to a nucleotide sequence containing a polymorphic site at which a SNP occurs. The term "polymorphic site" refers to a position of a polymorphic sequence at which a SNP occurs. The column labeled rs presents the SNP identification number of the SNP in the NCBI dbSNP database. The NCBI dbSNP database is publicly available and thus is easily accessible to those of ordinary skill in the art. In the present invention, the rs numbers are taken from NCBI dbSNP build 123. The column labeled SEQ ID NO. presents the sequence identification number for a 201 bp reference sequence for identification of the SNP in a nucleic acid and the columns labeled A1 and A2 present the two alleles occurring at the polymorphic site of the SNP, position 101 in each of these reference sequences. It should be understood that even though the reference sequence having a polymorphic site may contain changes at sites other than position 101, the polymorphic sequence is also within the scope of the present invention.

According to an embodiment of the method of the present invention, the determination of the nucleotide of the polymorphic site includes determining a genotype pattern of at least one multilocus marker selected from multilocus markers in Table 2 below. As used herein, the term "multilocus marker" refers to a genotype pattern that appears at a combination of multiple polymorphic sites that is associated with breast cancer.

TABLE 2

| ID | GP |
|---|---|
| Y01 | (013, 025, 034, 062) = (2–, 0, 2, 2) |
| Y02 | (025, 034, 064, 076) = (0, 2, 2–, 0–) |
| Y03 | (009, 022, 025, 060, 062) = (0–, 0–, 0, 0, 2) |
| Y04 | (008, 034, 042, 056, 062) = (1, 2, 2, 0, 0–) |
| Y05 | (008, 034, 042, 056, 068) = (1, 2, 2, 0, 0–) |
| Y06 | (022, 025, 035, 060, 072) = (0–, 0, 2, 0, 0) |
| Y07 | (006, 008, 018, 031, 048) = (1, 0–, 1, 2–, 0) |
| Y08 | (006, 008, 037, 071, 076) = (2–, 0–, 2–, 2–, 2) |
| Y09 | (006, 031, 034, 042, 060) = (2–, 0, 0–, 2, 0) |
| Y10 | (020, 025, 034, 056, 087) = (0, 0, 2, 0, 2) |
| Y11 | (003, 031, 061, 071, 076) = (2, 0, 1, 1, 2) |
| Y12 | (006, 018, 031, 048, 061) = (2–, 1, 0, 0, 0–) |
| Y13 | (006, 031, 048, 061, 076) = (2–, 0, 0, 1, 2) |
| Y14 | (009, 014, 034, 054, 064) = (2, 2, 0–, 2–, 1) |
| Y15 | (014, 018, 048, 064, 072) = (2, 0–, 0, 1, 0) |
| Y16 | (034, 037, 046, 061, 072) = (0–, 0, 2, 2–, 0) |

In Table 2, ID represents a multilocus marker name; and GP represents a genotype pattern of a multilocus marker, wherein each three-digit numbers in parentheses on the left side of an equal sign (=) represents "numbers" of SMBC_ numbers used to identify the polymorphic sequences of Table 1, and each one-digit number in parentheses on the right side of an equal sign represents a genotype of a polymorphic site of a polymorphic sequence of Table 1 corresponding to each corresponding three-digit numbers in parentheses on the left side of the equal sign, with: 0 being A1A1, 1 being A1A2, 2 being A2A2, 0– being A1A2 or A2A2, and 2– being A1A1 or A1A2 where A1 and A2 represent nucleotide alleles at a polymorphic site of each polymorphic sequence of Table 1. As each SNP has two possible alleles, the genotype of a SNP may exist in the form of a homozygote (e.g., A1A1) or a heterozygote (A1A2) in an individual.

The present invention also provides a method of diagnosing breast cancer in an. individual aged older than 54, which includes isolating a nucleic acid from the individual and determining a nucleotide of a polymorphic site of the nucleic acid, the determination of the nucleotide of the polymorphic site including determining a genotype of a polymorphic site (position 101) of at least one polymorphic sequence selected from polymorphic sequences in Table 3 below.

TABLE 3

| ID | rs | SEQ ID NO | A1 | A2 |
|---|---|---|---|---|
| SMBC_001 | rs1060442 | 1 | G | A |
| SMBC_003 | rs1020445 | 2 | G | A |
| SMBC_005 | rs1396953 | 3 | C | T |
| SMBC_006 | rs355510 | 4 | G | A |

TABLE 3-continued

| ID | rs | SEQ ID NO | A1 | A2 |
|---|---|---|---|---|
| SMBC_008 | rs1477454 | 5 | G | A |
| SMBC_009 | rs422679 | 6 | C | T |
| SMBC_010 | rs903501 | 7 | C | T |
| SMBC_011 | rs892005 | 8 | G | A |
| SMBC_013 | rs916380 | 9 | T | C |
| SMBC_014 | rs6791 | 10 | A | G |
| SMBC_016 | rs1559472 | 11 | A | G |
| SMBC_018 | rs729662 | 12 | A | G |
| SMBC_020 | rs1381067 | 13 | T | C |
| SMBC_022 | rs6668 | 14 | T | C |
| SMBC_025 | rs3824414 | 15 | T | C |
| SMBC_026 | rs3802368 | 16 | A | G |
| SMBC_031 | rs198550 | 17 | G | A |
| SMBC_034 | rs476476 | 18 | C | T |
| SMBC_035 | rs10699 | 19 | G | A |
| SMBC_042 | rs2303114 | 21 | T | C |
| SMBC_046 | rs2347597 | 22 | T | C |
| SMBC_048 | rs5277 | 23 | C | G |
| SMBC_054 | rs2077647 | 24 | C | T |
| SMBC_060 | rs2228480 | 26 | G | A |
| SMBC_061 | rs1372425 | 27 | C | T |
| SMBC_062 | rs841229 | 28 | G | A |
| SMBC_068 | rs1801132 | 30 | C | G |
| SMBC_071 | rs2518723 | 31 | T | C |
| SMBC_072 | rs12628 | 32 | T | C |
| SMBC_076 | rs2279901 | 33 | A | G |
| SMBC_083 | rs2291752 | 34 | C | T |
| SMBC_084 | rs1614984 | 35 | G | A |
| SMBC_087 | rs3731239 | 36 | C | T |
| SMBC_089 | rs2585175 | 37 | G | C |

In Table 3, the columns labeled ID, rs, SEQ ID NO, A1, and A2 are as defined above for Table 1.

In an embodiment of the method of the present invention, the determination of the nucleotide of the polymorphic site includes determining a genotype pattern of at least one multilocus marker selected from multilocus markers in Table 4 below.

TABLE 4

| ID | GP |
|---|---|
| O01 | (014, 031, 046, 076, 089) = (2, 2–, 1, 2, 1) |
| O02 | (006, 009, 025, 054, 061) = (0–, 2, 2–, 1, 0–) |

TABLE 4-continued

| ID | GP |
|---|---|
| O03 | (006, 026, 054, 061, 084) = (0–, 2, 1, 0–, 1) |
| O04 | (009, 042, 046, 083, 089) = (2, 0–, 1, 0, 2–) |
| O05 | (009, 046, 054, 062, 084) = (2, 2–, 0–, 0–, 0–) |
| O06 | (009, 046, 062, 084, 089) = (2, 2–, 0–, 0–, 2–) |
| O07 | (011, 016, 020, 054, 061) = (1, 2–, 2–, 1, 0–) |
| O08 | (011, 018, 048, 060, 072) = (1, 1, 0, 2–, 0) |
| O09 | (011, 035, 042, 089) = (2, 2–, 2–, 2–) |
| O10 | (006, 008, 018, 061, 084) = (0–, 2–, 0–, 0–, 0–) |
| O11 | (008, 009, 011, 018, 089) = (0–, 2, 1, 2–, 2–) |
| O12 | (010, 011, 018, 025, 054) = (2–, 2–, 2–, 1, 0–) |
| O13 | (011, 035, 054, 061, 089) = (2, 2–, 0–, 2–, 2–) |
| O14 | (013, 016, 061, 084, 087) = (0, 0–, 0–, 0–, 2) |
| O15 | (013, 034, 046, 061, 084) = (0, 0–, 2–, 0–, 0–) |
| O16 | (018, 022, 060, 061, 087) = (2–, 1, 2–, 0–, 0–) |
| O17 | (005, 034, 083, 089) = (2, 1, 0, 1) |
| O18 | (001, 003, 010, 011, 048) = (0, 2, 2–, 1, 0) |
| O19 | (006, 034, 054, 068, 084) = (1, 0–, 0–, 2–, 1) |
| O20 | (008, 009, 018, 061, 071) = (1, 2, 2–, 0–, 0–) |
| O21 | (009, 011, 016, 072, 084) = (2–, 1, 2–, 0, 2–) |
| O22 | (011, 013, 018, 020, 054) = (2–, 0–, 2–, 2–, 1) |
| O23 | (013, 034, 054, 061, 084) = (0, 0–, 0–, 0–, 0–) |
| O24 | (001, 006, 014, 061, 062) = (0, 2, 2, 0–, 0–) |

In Table 4, ID represents a multilocus marker name; and GP represents a genotype pattern of a multilocus marker, wherein each three-digit numbers in parentheses on the left side of an equal sign (=) represents "numbers" of SMBC_ numbers used to identify the polymorphic sequences of Table 3, and each one-digit number in parentheses on the right side of an equal sign represents a genotype of a polymorphic site of a polymorphic sequence of Table 3 corresponding to each corresponding three-digit numbers in parentheses on the left side of the equal sign, with: 0 being A1A1, 1 being A1A2, 2 being A2A2, 0– being A1A2 or A2A2, and 2– being A1A1 or A1A2 where A1 and A2 represent nucleotide alleles at a polymorphic site of each polymorphic sequence of Table 3.

In the method of the present invention, the individual may be selected from women belonging to any race. Preferably, the individual is a yellow race woman, and more preferably, a Korean woman.

In the method of the present invention, the nucleic acid, which is a chain of nucleotides, may be DNA, RNA, or a derivative thereof. Here, the term "DNA" includes, for example, biologically-derived DNA, synthetic or semisynthetic DNA, and cDNA derived from mRNA.

In the method of the present invention, the isolation of the nucleic acid from the individual can be carried out by any DNA isolation method known in the art. For example, the isolation of the nucleic acid can be achieved by directly purifying a target nucleic acid from a tissue or cell or by specifically amplifying a target nucleic acid by polymerase chain reaction (PCR) followed by purification. In addition to PCR, other methods include ligase chain reaction (LCR) (Wu and Wallace, *Genomics* 4, 560 (1989), Landegren et al., *Science* 241, 1077 (1988)), transcription amplification (Kwoh et al., *Proc. Natl. Acad. Sci. USA* 86, 1173 (1989)), self-sustained sequence replication (Guatelli et al., *Proc. Natl. Acad. Sci. USA* 87, 1874 (1990)), or nucleic acid sequence based amplification (NASBA).

The determination of the nucleotide of the polymorphic site of the nucleic acid can be carried out by any method known in the art. For example, a dideoxy method for direct nucleotide sequence determination or a hybridization method can be used. According to the hybridization method, a nucleic acid is allowed to hybridize with a probe having a polymorphic sequence, or its complement, and the degree of the hybridization is measured. For example, the measurement of the degree of the hybridization can be achieved by labeling target nucleic acids with a labeling material generating a detectable signal and specifically detecting hybridized target nucleic acids. Electrical signal detection may also be used.

In an embodiment of the method of the present invention, the determination of the nucleotide of the polymorphic site includes hybridizing the nucleic acid derived from the individual onto a microarray; and detecting the hybridization result. The microarray comprises probe polynucleotides comprising the nucleotides of one or more of the polymorphic sites of the SNP markers of Table 1 or 3, or the complement polynucleotides thereof, immobilized on a substrate.

A microarray is a substrate in which probes capable of specifically binding with target nucleic acids are immobilized onto specific regions of the substrate, and is widely used for rapid analysis of various biological samples. The length of the probes is not particularly limited, but may be 10 to 100 bp. A method of manufacturing a polynucleotide microarray is well known in the art. Any method of manufacturing a polynucleotide microarray known in the art may be used herein. Hybridization of nucleic acids on a microarray and detection of the hybridization result are also well known in the art. For example, the detection of the hybridization result can be performed by labeling a nucleic acid sample with a labeling material generating a detectable signal, such as a fluorescent material (e.g., Cy3 or Cy5), hybridizing the labeled nucleic acid sample onto a microarray, and detecting a signal generated from the labeling material.

As a result of the determination of the nucleotide of the polymorphic site, when the nucleic acid derived from the individual contains at least one risk allele, it may be determined that the individual has a higher likelihood of being diagnosed as a breast cancer patient or as at risk of developing breast cancer. In an embodiment of the method of the present invention, when the nucleic acid derived from the individual satisfies the genotype pattern of at least one of the multilocus markers of Table 2 or 4, it is determined that the individual has a higher likelihood of being diagnosed as a breast cancer patient or as at risk of developing breast cancer.

The present invention also provides a polynucleotide having the whole or a part of a polymorphic sequence selected from the group consisting of polymorphic sequences of Table 1 or Table 3 and wherein the part of the polymorphic sequence comprises a nucleotide at a polymorphic site (position 101) of the selected polymorphic sequence, or the complement of such a polynucleotide. The length of the polynucleotide is not particularly limited, but may be 10 to 201 bp, preferably 10 to 100 bp.

The polynucleotide of the present invention is specifically associated with breast cancer in a woman aged younger than 41 or older than 54. Thus, the polynucleotide can be effectively used in the diagnosis or treatment of breast cancer.

Herein, "a set of multilocus marker polynucleotides" means a set of polynucleotides including a polynucleotide for each of at least two of the respective SNP markers of a multilocus marker selected from the multilocus markers of Table 2, which are specifically associated with breast cancer in an individual aged younger than 41, or the multilocus markers of Table 4, which are specifically associated with breast cancer in an individual aged older than 54.

The polynucleotide can be used as a primer or a probe, but the present invention is not limited thereto. When using the polynucleotide as a probe, the polynucleotide may be in a solution or immobilized onto a solid substrate. For the latter, the polynucleotide may be used in the form of a microarray in which a polynucleotide array is deposited onto predetermined small regions.

The present invention also provides a microarray in which a polynucleotide having the whole or a part of a polymorphic sequence selected from the group consisting of the polymorphic sequences of Table 1 or Table 3 and wherein the part of the polymorphic sequence comprises a nucleotide of a polymorphic site (position 101) of the selected polymorphic sequence, or the complement of such a polynucleotide, is immobilized on a solid substrate. The microarray may include a set of multilocus marker polynucleotides for at least one multilocus marker of Table 2 or Table 4. The length of the polynucleotide is not particularly limited, but may be 10 to 201 bp, preferably 10 to 100 bp.

A microarray is well known in the art, and thus, the microarray of the present invention can be easily manufactured by those of ordinary skill in the art.

The present invention also provides a diagnostic kit for the detection of breast cancer, which includes a polynucleotide having the whole or a part of a polymorphic sequence selected from the group consisting of the polymorphic sequences of Table 1 or Table 3 and wherein the part of the polymorphic sequence comprises a nucleotide of a polymorphic site (position 101) of the polymorphic sequence, or the complement of such a polynucleotide, and a manufacturer's specification. The diagnostic kit may include a set of multilocus marker polynucleotides for at least one multilocus marker of Table 2 or Table 4. The length of the polynucleotide is not particularly limited, but may be 10 to 201 bp, preferably 10 to 100 bp.

In the diagnostic kit of the present invention, the polynucleotide contained in the diagnostic kit is as described above. The manufacturer's specification must state a method, materials, etc. to an extent that can be understood by those of ordinary skill in the art. For example, the diagnostic kit can be used in identifying a predetermined allele at a polymorphic site by hybridizing a nucleic acid sample derived from an individual onto the polynucleotide of the present invention used as a probe and measuring the degree of hybridization using a signal generated from the resultant hybrids. Based on the identification of predetermined allele or genotype, it can be determined if the individual has a likelihood of being diagnosed as at risk of developing breast cancer or as a breast cancer patient.

In the present invention, the polymorphic sequences (SNP markers) of Tables 1 and 3 and combinations of two or more of the polymorphic sequences are associated with breast cancer. The multilocus markers of Tables 2 and 4 are particularly associated with breast cancer. This was confirmed by DNA nucleotide sequence analysis of blood samples from breast cancer patients and normal persons. It is known that the incidence of breast cancer in women varies before and after menopause. Thus, the analyses of the genotype patterns of the multilocus markers were conducted in three age groups of the subjects which were classified based on the age of menopause. It is known that Korean women experience menopause at an average age of 47.6 and have menstrual transition for about 4 years. In this regard, the three age groups were as follows: young age group of 40 years or less, middle age group of 41-54 years, old age group of 55 years or more. The number of persons in each age group is presented in Table 5 below.

TABLE 5

| Group | Case | Normal | Total |
|---|---|---|---|
| Young | 87 | 90 | 177 |
| Middle | 117 | 120 | 237 |
| Old | 96 | 90 | 186 |

Occurrence frequency, odds ratio, and the 95% confidence interval (CI) of the odds ratio for each multilocus marker in the case group and the normal group are presented in Tables 6 and 7 below.

Table 6 shows the results for the young age group of 40 years or less. As shown in Table 6, the genotype patterns of the multilocus markers Y01 through Y16 specifically appeared in the case group, and the odds ratios of the multilocus markers Y01 through Y16 were more than 38. These results reveal that the multilocus markers Y01 through Y16 are positively associated with breast cancer.

TABLE 6

| ID | GP | #Case | #Control | OR | 95% CI |
|---|---|---|---|---|---|
| Y01 | (013, 025, 034, 062) = (2-, 0, 2, 2) | 20 | 0 | 54.97 | (3.27, 925.06) |
| Y02 | (025, 034, 064, 076) = (0, 2, 2-, 0-) | 19 | 0 | 51.53 | (3.06, 868.43) |
| Y03 | (009, 022, 025, 060, 062) = (0-, 0-, 0, 0, 2) | 19 | 0 | 51.53 | (3.06, 868.43) |
| Y04 | (008, 034, 042, 056, 062) = (1, 2, 2, 0, 0-) | 17 | 0 | 44.93 | (2.66, 760.06) |
| Y05 | (008, 034, 042, 056, 068) = (1, 2, 2, 0, 0-) | 17 | 0 | 44.93 | (2.66, 760.06) |
| Y06 | (022, 025, 035, 060, 072) = (0-, 0, 2, 0, 0) | 17 | 0 | 44.93 | (2.66, 760.06) |
| Y07 | (006, 008, 018, 031, 048) = (1, 0-, 1, 2-, 0) | 16 | 0 | 41.77 | (2.46, 708.17) |
| Y08 | (006, 008, 037, 071, 076) = (2-, 0-, 2-, 2-, 2) | 16 | 0 | 41.77 | (2.46, 708.17) |
| Y09 | (006, 031, 034, 042, 060) = (2-, 0, 0-, 2, 0) | 16 | 0 | 41.77 | (2.46, 708.17) |
| Y10 | (020, 025, 034, 056, 087) = (0, 0, 2, 0, 2) | 16 | 0 | 41.77 | (2.46, 708.17) |
| Y11 | (003, 031, 061, 071, 076) = (2, 0, 1, 1, 2) | 15 | 0 | 38.70 | (2.28, 657.74) |
| Y12 | (006, 018, 031, 048, 061) = (2-, 1, 0, 0, 0-) | 15 | 0 | 38.70 | (2.28, 657.74) |
| Y13 | (006, 031, 048, 061, 076) = (2-, 0, 0, 1, 2) | 15 | 0 | 38.70 | (2.28, 657.74) |
| Y14 | (009, 014, 034, 054, 064) = (2, 2, 0-, 2-, 1) | 15 | 0 | 38.70 | (2.28, 657.74) |
| Y15 | (014, 018, 048, 064, 072) = (2, 0-, 0, 1, 0) | 15 | 0 | 38.70 | (2.28, 657.74) |
| Y16 | (034, 037, 046, 061, 072) = (0-, 0, 2, 2-, 0) | 15 | 0 | 38.70 | (2.28, 657.74) |

In Table 6, ID and GP are as defined above in Table 2. #case and #control represent the occurrence frequency of each multilocus marker in the case group and the normal group, respectively. OR represents the odds ratio and 95% CI represents the 95% confidence interval for the odds ratio. 73 of the 87 cases satisfied the genotype pattern of at least one of the multilocus markers Y01 through Y16 (73/87=84%).

Table 7 shows the results for the old age group of 55 years or more. As shown in Table 7, the genotype patterns of the multilocus markers O01 through O24 specifically appeared in the case group, and the odds ratios of the multilocus markers O01 through O24 were more than 26. These results reveal that the multilocus markers O01 through O24 are positively associated with breast cancer.

TABLE 7

| ID | GP | #Case | #Control | OR | 95% CI |
|---|---|---|---|---|---|
| O01 | (014, 031, 046, 076, 089) = (2, 2-, 1, 2, 1) | 18 | 0 | 42.66 | (2.53, 719.39) |
| O02 | (006, 009, 025, 054, 061) = (0-, 2, 2-, 1, 0-) | 17 | 0 | 39.84 | (2.36, 673.28) |
| O03 | (006, 026, 054, 061, 084) = (0-, 2, 1, 0-, 1) | 17 | 0 | 39.84 | (2.36, 673.28) |
| O04 | (009, 042, 046, 083, 089) = (2, 0-, 1, 0, 2-) | 17 | 0 | 39.84 | (2.36, 673.28) |
| O05 | (009, 046, 054, 062, 084) = (2, 2-, 0-, 0-, 0-) | 17 | 0 | 39.84 | (2.36, 673.28) |
| O06 | (009, 046, 062, 084, 089) = (2, 2-, 0-, 0-, 2-) | 17 | 0 | 39.84 | (2.36, 673.28) |
| O07 | (011, 016, 020, 054, 061) = (1, 2-, 2-, 1, 0-) | 17 | 0 | 39.84 | (2.36, 673.28) |
| O08 | (011, 018, 048, 060, 072) = (1, 1, 0, 2-, 0) | 17 | 0 | 39.84 | (2.36, 673.28) |
| O09 | (011, 035, 042, 089) = (2, 2-, 2-, 2-) | 16 | 0 | 37.1 | (2.19, 628.33) |
| O10 | (006, 008, 018, 061, 084) = (0-, 2-, 0-, 0-, 0-) | 16 | 0 | 37.1 | (2.19, 628.33) |
| O11 | (008, 009, 011, 018, 089) = (0-, 2, 1, 2-, 2-) | 16 | 0 | 37.1 | (2.19, 628.33) |
| O12 | (010, 011, 018, 025, 054) = (2-, 2-, 2-, 1, 0-) | 16 | 0 | 37.1 | (2.19, 628.33) |
| O13 | (011, 035, 054, 061, 089) = (2, 2-, 0-, 2-, 2-) | 16 | 0 | 37.1 | (2.19, 628.33) |
| O14 | (013, 016, 061, 084, 087) = (0, 0-, 0-, 0-, 2) | 16 | 0 | 37.1 | (2.19, 628.33) |
| O15 | (013, 034, 046, 061, 084) = (0, 0-, 2-, 0-, 0-) | 16 | 0 | 37.1 | (2.19, 628.33) |
| O16 | (018, 022, 060, 061, 087) = (2-, 1, 2-, 0-, 0-) | 16 | 0 | 37.1 | (2.19, 628.33) |
| O17 | (005, 034, 083, 089) = (2, 1, 0, 1) | 15 | 0 | 34.42 | (2.03, 584.5) |
| O18 | (001, 003, 010, 011, 048) = (0, 2, 2-, 1, 0) | 15 | 0 | 34.42 | (2.03, 584.5) |
| O19 | (006, 034, 054, 068, 084) = (1, 0-, 0-, 2-, 1) | 15 | 0 | 34.42 | (2.03, 584.5) |
| O20 | (008, 009, 018, 061, 071) = (1, 2, 2-, 0-, 0-) | 15 | 0 | 34.42 | (2.03, 584.5) |
| O21 | (009, 011, 016, 072, 084) = (2-, 1, 2-, 0, 2-) | 15 | 0 | 34.42 | (2.03, 584.5) |
| O22 | (011, 013, 018, 020, 054) = (2-, 0-, 2-, 2-, 1) | 15 | 0 | 34.42 | (2.03, 584.5) |
| O23 | (013, 034, 054, 061, 084) = (0, 0-, 0-, 0-, 0-) | 24 | 1 | 29.67 | (3.92, 224.61) |
| O24 | (001, 006, 014, 061, 062) = (0, 2, 2, 0-, 0-) | 22 | 1 | 26.46 | (3.48, 200.98) |

In Table 7, ID, GP, OR, and 95% CI are as defined above for Table 6. 91 of the 96 casas satisfied the genotype pattern of at least one of the multilocus markers O01-O24 (91/96=94%).

The number of persons in each of the three age groups satisfying the genotype patterns of each of the multilocus markers Y01-Y16 and O01-O24 is presented in Table 8 below.

group and the normal group, respectively. FIG. 1 is a graph illustrating an odds ratio with respect to a multilocus marker in each of the young, middle, and old age groups. FIG. 1 shows that the multilocus markers Y01-Y16 are specific markers associated with breast cancer in an age group of 40 years or less, and the multilocus markers O01-O24 are specific markers associated with breast cancer in an age group of 55 years or more.

TABLE 8

| ID | Young | | | Middle | | | Old | | |
|---|---|---|---|---|---|---|---|---|---|
| | #Case | #Control | OR | #Case | #Control | OR | #Case | #Control | OR |
| Y01 | 20 | 0 | 53.73 | 9 | 14 | 0.63 | 9 | 10 | 0.83 |
| Y02 | 19 | 0 | 50.29 | 15 | 10 | 1.62 | 15 | 14 | 1.01 |
| Y03 | 19 | 0 | 50.29 | 8 | 14 | 0.56 | 8 | 12 | 0.59 |
| Y04 | 17 | 0 | 43.71 | 21 | 19 | 1.16 | 9 | 12 | 0.67 |
| Y05 | 17 | 0 | 43.71 | 12 | 14 | 0.87 | 6 | 12 | 0.43 |
| Y06 | 17 | 0 | 43.71 | 7 | 18 | 0.36 | 4 | 15 | 0.22 |
| Y07 | 16 | 0 | 40.56 | 11 | 15 | 0.73 | 13 | 10 | 1.25 |
| Y08 | 16 | 0 | 40.56 | 7 | 10 | 0.70 | 11 | 12 | 0.84 |
| Y09 | 16 | 0 | 40.56 | 11 | 8 | 1.45 | 9 | 12 | 0.67 |
| Y10 | 16 | 0 | 40.56 | 8 | 6 | 1.39 | 6 | 7 | 0.79 |
| Y11 | 15 | 0 | 37.50 | 7 | 8 | 0.89 | 9 | 9 | 0.93 |
| Y12 | 15 | 0 | 37.50 | 9 | 12 | 0.75 | 9 | 10 | 0.83 |
| Y13 | 15 | 0 | 37.50 | 8 | 9 | 0.91 | 8 | 10 | 0.73 |
| Y14 | 15 | 0 | 37.50 | 11 | 2 | 6.12 | 8 | 7 | 1.08 |
| Y15 | 15 | 0 | 37.50 | 11 | 12 | 0.93 | 8 | 11 | 0.65 |
| Y16 | 15 | 0 | 37.50 | 5 | 9 | 0.55 | 6 | 9 | 0.60 |
| O01 | 7 | 5 | 1.49 | 10 | 9 | 1.15 | 18 | 0 | 41.54 |
| O02 | 8 | 4 | 2.18 | 12 | 9 | 1.41 | 17 | 0 | 38.73 |
| O03 | 8 | 8 | 1.04 | 13 | 13 | 1.03 | 17 | 0 | 38.73 |
| O04 | 6 | 8 | 0.76 | 7 | 5 | 1.46 | 17 | 0 | 38.73 |
| O05 | 10 | 13 | 0.77 | 6 | 7 | 0.87 | 17 | 0 | 38.73 |
| O06 | 10 | 13 | 0.77 | 8 | 5 | 1.69 | 17 | 0 | 38.73 |
| O07 | 4 | 3 | 1.40 | 9 | 6 | 1.58 | 17 | 0 | 38.73 |
| O08 | 11 | 7 | 1.72 | 10 | 12 | 0.84 | 17 | 0 | 38.73 |
| O09 | 0 | 2 | 0.00 | 7 | 8 | 0.89 | 16 | 0 | 36.00 |
| O10 | 16 | 15 | 1.13 | 17 | 16 | 1.11 | 16 | 0 | 36.00 |
| O11 | 8 | 10 | 0.81 | 12 | 6 | 2.17 | 16 | 0 | 36.00 |
| O12 | 4 | 10 | 0.39 | 13 | 15 | 0.88 | 16 | 0 | 36.00 |
| O13 | 5 | 5 | 1.04 | 9 | 9 | 1.03 | 16 | 0 | 36.00 |
| O14 | 11 | 6 | 2.03 | 9 | 8 | 1.17 | 16 | 0 | 36.00 |
| O15 | 4 | 5 | 0.82 | 11 | 6 | 1.97 | 16 | 0 | 36.00 |
| O16 | 7 | 5 | 1.49 | 7 | 7 | 1.03 | 16 | 0 | 36.00 |
| O17 | 8 | 11 | 0.73 | 12 | 9 | 1.41 | 15 | 0 | 33.33 |
| O18 | 9 | 8 | 1.18 | 19 | 9 | 2.39 | 15 | 0 | 33.33 |
| O19 | 5 | 4 | 1.31 | 10 | 5 | 2.15 | 15 | 0 | 33.33 |
| O20 | 2 | 6 | 0.33 | 11 | 6 | 1.97 | 15 | 0 | 33.33 |
| O21 | 6 | 7 | 0.88 | 17 | 15 | 1.19 | 15 | 0 | 33.33 |
| O22 | 5 | 7 | 0.72 | 10 | 5 | 2.15 | 15 | 0 | 33.33 |
| O23 | 12 | 6 | 2.24 | 12 | 7 | 1.84 | 24 | 1 | 29.67 |
| O24 | 16 | 10 | 1.80 | 12 | 18 | 0.65 | 22 | 1 | 26.46 |

In Table 8, Young, Middle, and Old represent samples derived from the young age group of 40 years or less, the middle age group of 41-54 years, and the old age group of 55 years or more, respectively, OR represents the odds ratio, #case and #control represcent the number of persons satisfying the genotype pattern of each multilocus marker in the case The chi-square values and odds ratios for the individual SNP markers belonging to the multilocus markers Y01-Y16 in the young age group of 40 years or less are presented in Table 9 below.

TABLE 9

| ID | Delta | Chi-exact_pValue | OR | CI | con_HWE |
|---|---|---|---|---|---|
| SMBC_003 | 0.01 | 0.747 | 0.69 | (0.191, 2.492) | HWE |
| SMBC_006 | 0.04 | 0.542 | 1.28 | (0.754, 2.163) | HWE |
| SMBC_008 | 0.08 | 0.143 | 0.74 | (0.482, 1.121) | HWE |
| SMBC_009 | 0.03 | 0.837 | 0.89 | (0.578, 1.382) | HWE |
| SMBC_013 | 0.07 | 0.361 | 1.34 | (0.856, 2.108) | HWE |
| SMBC_014 | 0 | 0.767 | 0.97 | (0.52, 1.802) | HWE |
| SMBC_018 | 0.08 | 0.305 | 0.73 | (0.472, 1.116) | HWE |
| SMBC_020 | 0.06 | 0.398 | 0.73 | (0.449, 1.196) | HWE |

TABLE 9-continued

| ID | Delta | Chi-exact_pValue | OR | CI | con_HWE |
|---|---|---|---|---|---|
| SMBC_022 | 0.03 | 0.288 | 1.6 | (0.704, 3.637) | HWE |
| SMBC_025 | 0.13 | 0.046 | 1.73 | (1.113, 2.696) | HWE |
| SMBC_031 | 0.04 | 0.257 | 1.83 | (0.811, 4.119) | HWE |
| SMBC_034 | 0.06 | 0.349 | 0.71 | (0.425, 1.171) | HWE |
| SMBC_035 | 0 | 0.980 | 0.95 | (0.447, 2.008) | HWE |
| SMBC_037 | 0.03 | 0.514 | 0.87 | (0.561, 1.342) | HWE |
| SMBC_042 | 0.07 | 0.192 | 0.71 | (0.441, 1.144) | HWE |
| SMBC_046 | 0.03 | 0.773 | 0.86 | (0.538, 1.367) | HWE |
| SMBC_048 | 0.01 | 0.805 | 1.22 | (0.47, 3.169) | HWE |
| SMBC_054 | 0 | 0.988 | 1.02 | (0.649, 1.59) | HWE |
| SMBC_056 | 0.02 | 0.212 | 4.77 | (0.551, 41.25) | HWE |
| SMBC_060 | 0.05 | 0.178 | 1.38 | (0.806, 2.372) | HWE |
| SMBC_061 | 0.04 | 0.237 | 1.19 | (0.77, 1.836) | HWE |
| SMBC_062 | 0.03 | 0.523 | 0.86 | (0.547, 1.351) | HWE |
| SMBC_064 | 0.09 | 0.180 | 1.44 | (0.929, 2.219) | HWE |
| SMBC_068 | 0.02 | 0.884 | 0.93 | (0.608, 1.412) | HWE |
| SMBC_071 | 0.08 | 0.365 | 0.73 | (0.477, 1.127) | HWE |
| SMBC_072 | 0.07 | 0.273 | 1.54 | (0.897, 2.647) | HWE |
| SMBC_076 | 0.03 | 0.625 | 0.86 | (0.51, 1.438) | HWE |
| SMBC_087 | 0.01 | 0.665 | 0.88 | (0.46, 1.667) | HWE |

Table 9 shows that each SNP marker is associated with breast cancer. In Table 9, ID represents a SNP marker name, Delta represents the absolute value of the difference between the allele frequency of the case group and the allele frequency of the normal group. Here, the allele A2 frequency of the normal group is (genotype A2A2 frequency×2+genotype A1A2 frequency)/(the number of samples×2) in the normal group. Chi_exact_pValue represents the p-value determined using Fisher's exact test of chi-square test. When the number of genotypes is less than 5, results of the chi-square test may be inaccurate. Therefore, determination of the statistical significance (p-value) by the more accurate Fisher's exact test is desirable. In the present invention, when the p-value≦0.05, it is considered that the genotype of the case group is different from that of the normal group, i.e., there is a significant difference between the case group and the normal group. In Tables 6-9, the OR (odds ratio) represents the ratio of the probability of the risk allele in the case group to the probability of the risk allele in the normal group. In the present invention, the Mantel-Haenszel odds ratio method was used. CI represents 95% confidence interval for the odds ratio and is represented by (lower bound of the confidence interval, upper bound of the confidence interval). When 1 falls under the confidence interval, it is considered that there is insignificant association of risk allele with disease. HWE represents Hardy-Weinberg Equilibrium. According to Mendel's Law of inheritance and Hardy-Weinberg Law, the genetic makeup of alleles constituting a population is maintained at a constant frequency. When the genetic makeup is statistically significant, it can be considered to be biologically meaningful. Here, con_HWE represents the degree of deviation from the Hardy-Weinberg Equilibrium in the normal group. Based on a chi_value=6.63 (p-value=0.01, df=1) in a chi-square (df=1) test, a value larger than 6.63 was regarded as Hardy-Weinberg Disequilibrium (HWD) and a value smaller than 6.63 was regarded as Hardy-Weinberg Equilibrium (HWE).

The chi-square values and odds ratios for the individual SNP markers belonging to the multilocus markers O01-O24 in the old age group of 55 years or more are presented in Table 10 below.

TABLE 10

| ID | Delta | Chi_exact_pValue | OR | CI | con_HWE |
|---|---|---|---|---|---|
| SMBC_001 | 0.07 | 0.171 | 1.41 | (0.898, 2.229) | HWE |
| SMBC_003 | 0.03 | 0.311 | 1.8 | (0.652, 4.98) | HWE |
| SMBC_005 | 0.01 | 0.676 | 0.63 | (0.104, 3.801) | HWE |
| SMBC_006 | 0.01 | 0.656 | 0.93 | (0.571, 1.524) | HWE |
| SMBC_008 | 0.06 | 0.485 | 0.77 | (0.514, 1.166) | HWE |
| SMBC_009 | 0.03 | 0.271 | 0.87 | (0.566, 1.338) | HWE |
| SMBC_010 | 0.02 | 0.902 | 0.91 | (0.599, 1.376) | HWE |
| SMBC_011 | 0.05 | 0.032 | 1.25 | (0.789, 1.975) | HWE |
| SMBC_013 | 0 | 0.274 | 1.01 | (0.646, 1.572) | HWE |
| SMBC_014 | 0.01 | 0.613 | 1.05 | (0.57, 1.921) | HWE |
| SMBC_016 | 0.07 | 0.162 | 1.33 | (0.878, 2.008) | HWE |
| SMBC_018 | 0.03 | 0.366 | 1.15 | (0.742, 1.779) | HWE |
| SMBC_020 | 0.01 | 0.743 | 0.95 | (0.603, 1.507) | HWE |
| SMBC_022 | 0.03 | 0.233 | 1.59 | (0.729, 3.465) | HWE |
| SMBC_025 | 0.04 | 0.178 | 1.18 | (0.772, 1.819) | HWE |
| SMBC_026 | 0.01 | 0.836 | 0.88 | (0.402, 1.93) | HWE |
| SMBC_031 | 0.06 | 0.118 | 0.42 | (0.178, 0.982) | HWE |
| SMBC_034 | 0.01 | 0.973 | 1.05 | (0.646, 1.717) | HWE |
| SMBC_035 | 0.09 | 0.036 | 2.04 | (1.119, 3.712) | HWE |
| SMBC_042 | 0.07 | 0.308 | 1.41 | (0.893, 2.241) | HWE |
| SMBC_046 | 0.04 | 0.141 | 1.18 | (0.758, 1.834) | HWE |

TABLE 10-continued

| ID | Delta | Chi_exact_pValue | OR | CI | con_HWE |
|---|---|---|---|---|---|
| SMBC_048 | 0.05 | 0.025 | 4.06 | (1.114, 14.81) | HWE |
| SMBC_054 | 0.07 | 0.047 | 0.75 | (0.49, 1.151) | HWE |
| SMBC_060 | 0.02 | 0.901 | 0.89 | (0.532, 1.487) | HWE |
| SMBC_061 | 0.1 | 0.163 | 0.68 | (0.45, 1.026) | HWE |
| SMBC_062 | 0.01 | 0.920 | 1.02 | (0.659, 1.586) | HWE |
| SMBC_068 | 0.01 | 0.883 | 1.03 | (0.687, 1.558) | HWE |
| SMBC_071 | 0.1 | 0.191 | 0.67 | (0.442, 1.014) | HWE |
| SMBC_072 | 0.04 | 0.148 | 1.32 | (0.771, 2.247) | HWE |
| SMBC_076 | 0.01 | 0.790 | 1.04 | (0.62, 1.729) | HWE |
| SMBC_083 | 0.03 | 0.578 | 1.18 | (0.724, 1.913) | HWE |
| SMBC_084 | 0.01 | 0.338 | 0.96 | (0.621, 1.47) | HWE |
| SMBC_087 | 0.02 | 0.800 | 0.89 | (0.517, 1.53) | HWE |
| SMBC_089 | 0.06 | 0.161 | 1.27 | (0.835, 1.938) | HWE |

Table 10 shows that each SNP marker is associated with breast cancer. Column labels are as defined for Table 9.

Information about the individual SNP markers belonging to the multilocus markers Y01-Y16 and O01-O24 of the present invention are summarized in Table 11 below.

TABLE 11

| rs | ID | Band | Gene | fxn class | aa_residue | aa_position |
|---|---|---|---|---|---|---|
| rs1060442 | SMBC_001 | 19p13.3 | THRAP5 | coding-synon | F | 277 |
| rs1020445 | SMBC_003 | 2p21 | PRKCE | Intron | null | |
| rs1396953 | SMBC_005 | 2q34 | LANCL1 | Intron | null | |
| rs355510 | SMBC_006 | 4q13.2 | CENPC1 | coding-synon | S | 232 |
| rs1477454 | SMBC_008 | 2q32.1 | LOC389066 | Intron | null | |
| rs422679 | SMBC_009 | 17p13.1 | RPL26 | Intron | null | |
| rs903501 | SMBC_010 | 17q12 | CAB2 | Intron | null | |
| rs892005 | SMBC_011 | 5q33.1 | G3BP | Intron | null | |
| rs916380 | SMBC_013 | 1p36.22 | | Intergenic | n/a | n/a |
| rs6791 | SMBC_014 | 19p13.2 | STXBP2 | coding-nonsynon | V→I | 526 |
| rs1559472 | SMBC_016 | 2p23.3 | ITSN2 | Intron | null | |
| rs729662 | SMBC_018 | 11p15.4 | CARS | Coding-synon | P | 623 |
| rs1381067 | SMBC_020 | 3q13.31 | LSAMP | Intron | null | |
| rs6668 | SMBC_022 | 7p15.2 | | Intergenic | n/a | n/a |
| rs3824414 | SMBC_025 | 9q33.3 | SLC2A8 | Intron | null | |
| rs3802368 | SMBC_026 | 9q33.3 | SLC2A8 | Intron | null | |
| rs198550 | SMBC_031 | 17q21.33 | CACNA1G | Intron | null | |
| rs476476 | SMBC_034 | 18p11.32 | KIAA0650 | Intron | null | |
| rs10699 | SMBC_035 | 5q12.3 | ARFD1 | mrna-utr, intron | null | |
| rs736869 | SMBC_037 | 2p25.3 | D2S448 | Intron | null | |
| rs2303114 | SMBC_042 | 19p13.2 | | Intergenic | n/a | n/a |
| rs2347597 | SMBC_046 | 5q33.1 | G3BP | Intron | null | |
| rs5277 | SMBC_048 | 1q31.1 | PTGS2 | coding-synon | V | 102 |
| rs2077647 | SMBC_054 | 6q25.1 | ESR1 | coding-synon | S | 10 |
| rs3218625 | SMBC_056 | 1q31.1 | PTGS2 | coding-nonsynon | R | 587 |
| rs2228480 | SMBC_060 | 6q25.2 | ESR1 | coding-synon | T | 594 |
| rs1372425 | SMBC_061 | 3p12.3 | ROBO2 | Intron | null | |
| rs841229 | SMBC_062 | 16p13.3 | MGRN1 | Intron | null | |
| rs355499 | SMBC_064 | 4q13.2 | CENPC1 | Intron | null | |
| rs1801132 | SMBC_068 | 6q25.1 | ESR1 | coding-synon | P | 325 |
| rs2518723 | SMBC_071 | 9p21.3 | CDKN2A | locus-region | null | |
| rs12628 | SMBC_072 | 11p15.5 | HRAS | coding-synon | H | 27 |
| rs2279901 | SMBC_076 | 11p15.1 | TSG101 | coding-synon | D | 236 |
| rs2291752 | SMBC_083 | 11p15.1 | TSG101 | locus-region | null | |
| rs1614984 | SMBC_084 | 17p13.1 | TP53 | locus-region | null | |
| rs3731239 | SMBC_087 | 9p21.3 | CDKN2A | intron, mrna-utr | null | |
| rs2585175 | SMBC_089 | 8q24.3 | HSJ001348 | locus-region | null | |

In Table 11, "Band" indicates the chromosome number of the SNP, where "p" is the short arm of the chromosome from the centromere, "q" is the long arm from the centromere, and the numbers are the band numbers. For example, when the number of SNP positioned in ID: SMBC_001 is 19p13.3, the SNP is located in the short arm (p) of the 19th chromosome and in the band 13.3 region. "Gene" refers to a gene including the SNP. "fxn_class" indicates a role performed by the SNP within the gene. "aa_residue" indicates the amino acid of the SNP. "aa_position" indicates the position of the amino acid in the protein produced from the gene.

EXAMPLES

Considering the report that Korean women experience menopause at an average age of 47.6 and have menstrual transition for about 4 years, subjects were classified into three age groups: young age group of 40 years or less, middle age group of 41-54 years, old age group of 55 years or more. DNA samples were extracted from blood streams of the subjects, and occurrence frequencies of SNPs were analyzed. The number of persons belonging to each age group is presented in the above Table 5.

A case group consisted of persons that had been identified as breast cancer patients and had been under treatment and a normal group consisted of persons free from symptoms of breast cancer and of the same age as the case group. SNPs used in the Examples were selected from a public database (NCBI dbSNP:http://www.ncbi.nlm.nih.gov/SNP/) (see Tables 1 and 3). Primers hybridizing with sequences around the selected SNPs were used to assay the nucleotide sequences of SNPs in the DNA samples.

1. Preparation of DNA Samples

DNA samples were extracted from blood samples of breast cancer patients and normal persons. The DNA extraction was performed according to a known extraction method (Molecular cloning: A Laboratory Manual, p 392, Sambrook, Fritsch and Maniatis, 2nd edition, Cold Spring Harbor Press, 1989) and the instructions of a commercial kit manufactured by Gentra system. Among extracted DNA samples, only DNA samples having a purity ($A_{260}/A_{280}$ nm) of at least 1.7 were used.

2. Amplification of Target DNAs

Target DNAs, which were predetermined DNA regions containing the SNPs to be analyzed, were amplified by PCR. The PCR was performed by a common method at the following conditions. First, 2.5 ng/ml of target genomic DNA was prepared. Then, the following PCR mixture was prepared.

| | |
|---|---|
| Water (HPLC grade) | 2.24 μL |
| 10x buffer (15 mM $MgCl_2$, 25 mM $MgCl_2$) | 0.5 μL |
| dNTP Mix (GIBCO) (25 mM for each) | 0.04 μL |
| Taq pol (HotStar) (5 U/μL) | 0.02 μL |
| Forward/reverse primer Mix (1 μM for each) | 0.02 μL |
| DNA | 1.00 μL |
| Total volume | 5.00 μL |

Here, the forward and reverse primers were designed based on the known upstream and downstream sequences of the SNPs in the database. The sequence identification numbers of the forward and reverse amplification primers are listed in Table 12 below.

The thermal cycles of PCR were as follows: incubation at 95□ for 15 minutes; 45 cycles at 95° C. for 30 seconds, at 56° C. for 30 seconds, and at 72° C. for 1 minute; and incubation at 72° C. for 3 minutes and storage at 4° C.

3. Analysis of SNPs in Amplified Target DNA Fragments

Analysis of a SNP in the amplified target DNA fragments was performed using a homogeneous MassExtension (hME) technique available from Sequenom. The principle of the MassExtension technique was as follows. First, a primer (also called an "extension primer") ending immediately before the SNP within the target DNA fragments was designed. Then, the primer was hybridized with the target DNA fragments and DNA polymerization was performed. At this time, the polymerization solution contained a reagent (e.g., ddTTP) terminating the polymerization immediately after the incorporation of a nucleotide complementary to a first allelic nucleotide (e.g., A allele). In this regard, if the first allele (e.g., A allele) exists in the target DNA fragments, products in which only a nucleotide (e.g., T nucleotide) complementary to the first allele is extended from the primers will be obtained. On the other hand, if a second allele (e.g., G allele) exists in the target DNA fragments, a nucleotide (e.g., C nucleotide) complementary to the second allele is added to the 3'-ends of the primers and then the primers are extended until a nucleotide complementary to the closest first allele nucleotide (e.g., A nucleotide) is added. The lengths of products extended from the primers were determined by mass spectrometry, thereby permitting identification of the alleles present in the target DNA fragments. Illustrative experimental conditions were as follows.

First, unreacted dNTPs were removed from the PCR products. For this, 1.53 μL of deionized water, 0.17 μL of hME buffer, and 0.30 μL of shrimp alkaline phosphatase (SAP) were added and mixed in 1.5 ml tubes to prepare SAP enzyme solutions. The tubes were centrifuged at 5,000 rpm for 10 seconds. Thereafter, the PCR products were added to the SAP solution tubes, sealed, incubated at 37° C. for 20 minutes and then 85° C. for 5 minutes, and stored at 4° C.

Next, homogeneous extension was performed using the amplified target DNA fragments as templates. The composition of the reaction solutions for the extension were as follows.

| | |
|---|---|
| Water (deionized water) | 1.728 μL |
| hME extension mix (10x buffer containing 2.25 mM d/ddNTPs) | 0.200 μL |
| Extension primers (100 μM for each) | 0.054 μL |
| Thermosequenase (32 U/μL) | 0.018 μL |
| Total volume | 2.00 μL |

The reaction solutions were thoroughly stirred and subjected to spin-down centrifugation. Tubes or plates containing the resultant solutions were compactly sealed and incubated at 94° C. for 2 minutes, followed by 40 thermal cycles at 94° C. for 5 seconds, at 52° C. for 5 seconds, and at 72° C. for 5 seconds, and storage at 4° C. The homogeneous extension products thus obtained were purified with a resin (SpectroCLEAN from Sequenom).

Nucleotides of polymorphic sites in the extension products were assayed using mass spectrometry, MALDI-TOF (Matrix Assisted Laser Desorption and Ionization-Time of Flight). The MALDI-TOF is operated according to the following principle. When an analyte is exposed to a laser beam, it flies toward a detector positioned at the opposite side in a vacuum state, together with an ionized matrix. At this time, the time taken for the analyte to reach the detector is calculated. A material with a smaller mass reaches the detector more rapidly. The nucleotides of SNPs in the target DNA fragments are determined based on a difference in mass between the DNA fragments and known SNP sequences. The sequence identification numbers of the extension primers used in this study for the extension of target DNAs are also listed in Table 12 below.

TABLE 12

| Marker name | Amplification primer (SEQ ID NO) Forward primer | Reverse primer | Extension primer (SEQ ID NO) |
|---|---|---|---|
| SMBC_001 | 38 | 39 | 40 |
| SMBC_003 | 41 | 42 | 43 |
| SMBC_005 | 44 | 45 | 46 |
| SMBC_006 | 47 | 48 | 49 |
| SMBC_008 | 50 | 51 | 52 |
| SMBC_009 | 53 | 54 | 55 |
| SMBC_010 | 56 | 57 | 58 |
| SMBC_011 | 59 | 60 | 61 |
| SMBC_013 | 62 | 63 | 64 |
| SMBC_014 | 65 | 66 | 67 |
| SMBC_016 | 68 | 69 | 70 |
| SMBC_018 | 71 | 72 | 73 |
| SMBC_020 | 74 | 75 | 76 |
| SMBC_022 | 77 | 78 | 79 |
| SMBC_025 | 80 | 81 | 82 |
| SMBC_026 | 83 | 84 | 85 |
| SMBC_031 | 86 | 87 | 88 |
| SMBC_034 | 89 | 90 | 91 |
| SMBC_035 | 92 | 93 | 94 |
| SMBC_037 | 95 | 96 | 97 |
| SMBC_042 | 98 | 99 | 100 |
| SMBC_046 | 101 | 102 | 103 |
| SMBC_048 | 104 | 105 | 106 |
| SMBC_054 | 107 | 108 | 109 |
| SMBC_056 | 110 | 111 | 112 |
| SMBC_060 | 113 | 114 | 115 |
| SMBC_061 | 116 | 117 | 118 |
| SMBC_062 | 119 | 120 | 121 |
| SMBC_064 | 122 | 123 | 124 |
| SMBC_068 | 125 | 126 | 127 |
| SMBC_071 | 128 | 129 | 130 |
| SMBC_072 | 131 | 132 | 133 |
| SMBC_076 | 134 | 135 | 136 |
| SMBC_083 | 137 | 138 | 139 |
| SMBC_084 | 140 | 141 | 142 |
| SMBC_087 | 143 | 144 | 145 |
| SMBC_089 | 146 | 147 | 148 |

The results for the determination of polymorphic sequences of the target DNAs using the MALDI-TOF are presented in the above Tables 6-11.

SNP markers and multilocus markers associated with breast cancer according to the present invention can be used in determining if an individual has a higher or lower likelihood of being diagnosed as a breast cancer patient or as at risk of developing breast cancer. Furthermore, individuals can be classified into several subgroups according to the absence or presence of at least one of the SNP markers, and the SNP markers and the multilocus markers are suitable for assaying sensitivities to breast cancer therapeutic or preventive drugs according to the subgroups. In addition, the SNP markers and multilocus markers can be used in the prediction or verification of the prognosis of breast cancer, development of breast cancer preventive or therapeutic drugs, etc.

According to the method of the present invention, the presence of or a risk of breast cancer can be effectively detected in an individual aged younger than 41 or older than 54.

The polynucleotide, microarray and diagnostic kit of the present invention can be effectively used in the detection of the presence of or a risk of breast cancer in an individual aged younger than 41 or older than 54.

Any combination of the above-described elements in all possible variations thereof is encompassed by the invention unless otherwise indicated herein or otherwise clearly contradicted by context.

What is claimed is:

1. A method of determining an increased risk of having or developing breast cancer in a human female aged younger than 41, which comprises
   a) obtaining a nucleic acid sample from the human female aged younger than 41;
   b) determining the nucleotide present at position 101 of SEQ ID NO: 9 (SMBC_013); the nucleotide present at position 101 of SEQ ID NO: 15 (SMBC_025); the nucleotide present at position 101 of SEQ ID NO: 18 (SMBC_034); and the nucleotide present at position 101 of SEQ ID NO: 28 (SMBC_062); and
   c) determining that the female has an increased risk of having breast cancer or developing breast cancer when a TT or TO is determined at SMBC_013; TT is determined at SMBC_25; TT is determined at SMBC_034; and AA is determined at SMBC_062 compared to when a different genotype pattern is determined to be present.

2. The method of claim 1, wherein determining the nucleotides present comprises hybridizing the nucleic acid from the human female aged younger than 41 to a microarray, wherein the microarray comprises a probe polynucleotide for determining the nucleotide present at position 101 of SEQ ID NO: 15 (SMBC_025); the nucleotide at position 101 of SEQ ID NO: 18 (SMBC_034); and the nucleotide at position 101 of SEQ ID NO: 28 (SMBC_062), or a complement thereof; and
   detecting the hybridization result.

* * * * *

SEQUENCE LISTING

```
<160> NUMBER OF SEQ ID NOS: 148

<210> SEQ ID NO 1
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 1
cagtgcttca ttccaagcct gccagcccac gtgatggcct gcgcccgttc acctgctccg      60
acatgtcccg ggccaggaac ttgaggtggg tgatggcggg naacttgtcc ttgcggttga     120
ggtcggtggt gcagcgcatg aacagggagg gcaggatctc cgtgtcgata cggcacttct     180
cgctcaccac gctcacgcac a                                                201

<210> SEQ ID NO 2
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 2
gagagtgact gtgcctcatt atatacagat atcagagatg ttcactgtga accactccaa      60
taggttgcct ttcctgaaag ttgtttggga tgttttgctc ngcatgaagt gtttgtttgc     120
cttattcctg cccaaactga gagataacta gtgtgatgtg attcagattt aagacatggc     180
ctgtcataga caatcaaaat g                                                201

<210> SEQ ID NO 3
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site

<400> SEQUENCE: 3
agttcaaggg catttaaaga ctcccttcat gtactctggt agggaaaatc atgttcagat      60
tttagatcta caaggctcac tggaggtgct taactaacac ncattagttt agaatgacat     120
```

```
ggagacagga acttcccaaa ggaggggggca cttgggtgtt ccaatctaag ttcaaataca    180
tttttcccta cttgaaacgt t                                              201
```

<210> SEQ ID NO 4
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 4

```
taccctcctt ttaacctttt aggttaaact ttgatgataa agttatgtta aagaaaatag    60
aaatagataa taaagtatca gatgaagagg ataaaacatc ngaaggacaa gaaagaaaac   120
catcaggatc atctcagaat agaatacgag attcagaata tgaaattcaa cgacaagcta   180
aaaaaagttt ttcaacattg t                                             201
```

<210> SEQ ID NO 5
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 5

```
ccatgatcag aaatagcagt cccagaacat tcaagattac ttgaatatgc aactttgctg    60
aattgactgt agtcagtgac tgaagaattc attagtactc ngaagcactc tggtgcttgc   120
agacttcaag aactattttt atacccaagc tacaataatt tgtttagacc ctcagtctcc   180
tccctaatac tgtctctagg g                                             201
```

<210> SEQ ID NO 6
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site

<400> SEQUENCE: 6

```
gaaaagcagc ttacttactg ttttttggtc cctggctcaa ctcatcttgc cactctttgg    60
gagcaagagt ctcagaagca tctttctcag gaatgcaatc nctcttctaa gctaagtgcg   120
taaaatatcc atcaagacaa cgagaacaag tagggataca cacctgaact tcatcatcct   180
ttcggatggg catggatcgc a                                             201
```

<210> SEQ ID NO 7
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site

<400> SEQUENCE: 7

```
ctccaatgtg aggctctcca tggctggccc catccaccac ccatcagtcc gcccagctca    60
cacccactct ctgatttcct gcatgtcagg ctgcctggaa ngaccctccc tctctcccac   120
```
ctgggcactt tctgagactt ctctttagaa gccttccctt actcttctca aatttaccta    180
gttaacattc atgcatcctt c    201

<210> SEQ ID NO 8
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 8
aaagtgcagt ttattccaac atgttcaggt aatttattca ttattttcaa ccattattaa    60
aagacttgcc tgggggttta ggaaaacaaa ccttatgttt nagtaactta gttttgaaa    120 acatgaatta tgagaatgag aaaatgaata gttatcagtg cactgagatt tacgtaacta    180
cctttccttg gtggtggctt t    201

<210> SEQ ID NO 9
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t

<400> SEQUENCE: 9
aagagctgga ctctggagtc agaaaggtct gagttcaaat cccacccctg ctgctgagag    60
agtggcacag ggcagtttca ccactgtgag cttgttcctc ntctgtgaac tgaataataa    120
accctgcttt ccagaaaaga ggcgcacaga gaggacttta tcatagggcc cacgatgagc    180 tcccgggtc ngagcganag a    201

<210> SEQ ID NO 10
<211> LENGTH: 201
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: variation
<222> LOCATION: (101)
<223> OTHER INFORMATION: n=A or G, polymorphic site

<400> SEQUENCE: 10
aggtgggcgg cctggcngcg gtgagggcct cctgcctgga ctttctgccc ctgccctgca    60
cagtgcccgc ttcggtcact ggcacaagaa caaggctggc ntagaagccc gggcgggccc    120
ccggctcatc gtgtatgtca tgggcggtgt ggccatgtca gagatgaggg ccgcctacga    180
ggtgaccagg gccaccgagg g    201

<210> SEQ ID NO 11

<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 11

| | |
|---|---|
| acctaccagg tcctatgctt ggtgaactga attctaaagg caaaaaaggt ttaggataaa | 60 |
| tattctgaat gccaattagc ccaaagcaat gaaaaagcaa ncaaggccct tactctaact | 120 |
| cttttttatg tctaagtgat ataattattc ccttacacac ccttctactc tgtcacacac | 180 |
| acaattagga ccttgtatct a | 201 |

<210> SEQ ID NO 12
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 12

| | |
|---|---|
| gggagctctc cttgtgacac ctctccaagc tcctggtaac tttgtagcaa acagcaaggg | 60 |
| ctcacccacc ttcgtggtct tcaaaccgca ccccaagctc nggcaggatg ttgtcccgca | 120 |
| gggcatcgct gagctgcaga atctcaggga ctgtaggaga agcagagcag ttccctcaga | 180 |
| catggaggag ccagggccca c | 201 |

<210> SEQ ID NO 13
<211> LENGTH: 201
<212> TYPE: DNA
<213> ORGANISM: Homo sapiens
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: variation
<222> LOCATION: (101)
<223> OTHER INFORMATION: n=C or T, polymorphic site

<400> SEQUENCE: 13

| | |
|---|---|
| gcttggattc agggtagaag aaangattag agaaggtcct acaatgcatt ttggtgtaag | 60 |
| tttttaagtg gcctatatca ttacaaaagg agtcatgatc nccctttta ataattgcag | 120 |
| aaccccaatt ttccttttgt acttttgtc atggggtgat atcagattca tcacatgtaa | 180 |
| atgacaagta aaagagacat t | 201 |

<210> SEQ ID NO 14
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site

<400> SEQUENCE: 14

| | |
|---|---|
| gcggccgccc ttctccgctt actgttcccg gctccccgca ggccgggtgc tcgcagccgg | 60 |
| gctggctatg cctcgcctgg cagcccagag cgccgctccc ngggaacagc acacaaaggc | 120 |
| agcctcccct ggcctctagc ccttaggctt ctgtagctca gttctttccc cacacccctc | 180 |

```
ccccaagaaa ttctgggggc c                                              201

<210> SEQ ID NO 15
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site
<220> FEATURE:
<221> NAME/KEY: misc_feature
<222> LOCATION: (201)..(201)
<223> OTHER INFORMATION: n is a, c, g, or t

<400> SEQUENCE: 15
gtgaggcctt cagcaagagc tgcggcccac ggacatttgg tacccagcag ctgctgcgaa    60
gacgaccgtc ggggctgagg gttactcgct gctgcttctg ngccggtacc tcccatttcc   120
tcggcccaga gggtctgctc cgggaacttt ttgcagttcg ctgaggtcca aggcggggtg   180
gctgccaccc agtcagggct n                                              201

<210> SEQ ID NO 16
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 16
atgtccgcgt tgtcataccc actgtcgctt ccgcagctgg tgtgattggc ccgtgccatg    60
tgccttcatg aacagttgtg ataatggcaa tgtcagtagc naacatgagg gcagatgtgc   120
agaggcagcg aggccccatc tctgaagctg agtctttgag gctggcaagg cccaggctgg   180
ctcaccctgg ctctgacgcc a                                              201

<210> SEQ ID NO 17
<211> LENGTH: 201
<212> TYPE: DNA
<213> ORGANISM: Homo sapiens
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: variation
<222> LOCATION: (101)
<223> OTHER INFORMATION: n=A or G, polymorphic site

<400> SEQUENCE: 17
aaatgagata atgcttggaa ataactgag cntggcgctt ggctcatagg aatgcctccg    60
tatgtggtgg ctggcattgt gattcacttt tcttcaggac ntttcctctt cctgtcccca   120
cccctacagg tgggctcctt cttcatgatc aacctgtgcc tggtggtgat tgccacgcag   180
ttctcagaga ccaagcagcg g                                              201

<210> SEQ ID NO 18
<211> LENGTH: 201
<212> TYPE: DNA
<213> ORGANISM: Homo sapiens
<220> FEATURE:
<221> NAME/KEY: variation
<222> LOCATION: (101)
```

<223> OTHER INFORMATION: n=C or T, polymorphic site
<220> FEATURE:
<221> NAME/KEY: misc_feature
<222> LOCATION: (198)..(198)
<223> OTHER INFORMATION: n is a, c, g, or t

<400> SEQUENCE: 18
attgcttttc agaattaatc acatgatctg atttatatgt tacttttaaa cgataatggc      60
cacagtgata cttttgtggc agagctctaa agaaatgact naagaatttt tattttatct    120
cactaaaaaa atagggcaat attaacaaca aagacaaaga ggatgccttt gtatcatatt    180
agtatatgaa ccacaccnttt t                                              201

<210> SEQ ID NO 19
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 19
aaacagtaaa gagcacacat ttttatttac tcacaacact gaataattaa tgtaaacttt      60
ttgaattttt tttttcttta gacattttttc ctctagagta nctttcaag gccttctcat    120 gaacagcctt aagttttatt gtcaaaataa atgcacttat tttgggaaac agtttgaagt    180
aagtaataag catttgccac t                                               201

<210> SEQ ID NO 20
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site
<220> FEATURE:
<221> NAME/KEY: misc_feature
<222> LOCATION: (135)..(135)
<223> OTHER INFORMATION: n is a, c, g, or t

<400> SEQUENCE: 20
gagaagcttc gcgtaggccc cagggtcccg agccccgagt ctcgagcgca gaatcagggg      60
tgccaatgct ctcctccgcg cccccgagcg ctcgccttgg ncatgcgggc cgccccaccg    120
ggatgagggc gctcnggccg gacgctgggg ccccgggttc tcgccccgcc ccgccctcgg    180
ggattcagag gggccgggag g                                               201

<210> SEQ ID NO 21
<211> LENGTH: 201
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: variation
<222> LOCATION: (101)
<223> OTHER INFORMATION: n=C or T, polymorphic site

<400> SEQUENCE: 21
tgcccngcct gtagggctcg gggacctcca gccggctgga gccgagagaa cgcatggagc      60
ccacctatca gctgtcccgc tggaccccgg tcatcaagga ngtaatggag gtactgggtg    120
gcaggtcagg gtgggggcca gccctccgca tcggctggcg gctcagcctc cctcctgctg    180
aggtgctaag cctcagggct t                                              201

<210> SEQ ID NO 22
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site
<220> FEATURE:
<221> NAME/KEY: misc_feature
<222> LOCATION: (190)..(190)
<223> OTHER INFORMATION: n is a, c, g, or t

<400> SEQUENCE: 22
agtcattcct tgtacctgtc tcccaacccc tggcagccac taatctgctt tctgtcccta    60
tgaattaaaa ttgtgtactt taaaccatat aataaaaata ntgcagatca gtgatattct    120
ccagaatgtt aatgggcata ctgcaaagtt ttttatttttt ttattttttt ttttttgaga    180
cagtgtctcn ctctgccacc c                                              201

<210> SEQ ID NO 23
<211> LENGTH: 201
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: variation
<222> LOCATION: (101)
<223> OTHER INFORMATION: n=C or G, polymorphic site

<400> SEQUENCE: 23
cttggaaata tgttttttaga ttaggcttac agtattataa agcatatttt tctttgagaa   60
ngctaaaaac cttagaaaga cacttgtact tacatgtcaa nacataactc ataattgcat   120
ttcgaaggaa gggaatgtta ttcacaacgt tccaaaatcc cttgaagtgg gtaagtatgt   180
agtgcactgt gtttggagtg g                                              201

<210> SEQ ID NO 24
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site

<400> SEQUENCE: 24
ggtggcccgc cggtttctga gccttctgcc ctgcgggac acggtctgca ccctgcccgc     60
ggccacggac catgaccatg accctccaca ccaaagcatc nggatggcc ctactgcatc    120 agatccaagg gaacgagctg gagcccctga accgtccgca gctcaagatc ccctggagc    180 ggcccctggg cgaggtgtac c                                              201

<210> SEQ ID NO 25
<211> LENGTH: 201
<212> TYPE: DNA
<213> ORGANISM: Homo sapiens
<220> FEATURE:

```
<221> NAME/KEY: variation
<222> LOCATION: (101)
<223> OTHER INFORMATION: n=C or T, polymorphic site
<220> FEATURE:
<221> NAME/KEY: misc_feature
<222> LOCATION: (105)..(105)
<223> OTHER INFORMATION: n is a, c, g, or t

<400> SEQUENCE: 25
atagacatgg ttcatataaa taaataaata tgatcattag acttctacag ttcagtcgaa      60
cgttctttta gtagtactgt gggattgata tcatctagtc nggancggga agaacttgca     120
ttgatggtga ctgttttaat gagctctgga tctggaacac tgaatgaagt aaagggacag     180
cccttcacgt tattgcagat g                                                201

<210> SEQ ID NO 26
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 26
aggagacgga ccaaagccac ttggccactg cgggctctac ttcatcgcat tccttgcaaa      60
agtattacat cacggggggag gcagagggtt tccctgccac ngtctgagag ctccctggct    120
cccacacggt tcagataatc cctgctgcat tttaccctca tcatgcacca ctttagccaa     180
attctgtctc ctgcatacac t                                                201

<210> SEQ ID NO 27
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site

<400> SEQUENCE: 27
aggtgtcttc cttggaatct tgagacaaca tcactgcaag caagaagcag acatctattg      60
ctaaactaaa gttgaatttt tgtatctact ccttttcccc ntttctgggc atggctcttg    120
gtagatttag cagcaattta gagagcctgg gggagtgtag aagaccaca ggtttcacca     180 gtgcatagcc catctgtaga a                                                201

<210> SEQ ID NO 28
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site

<400> SEQUENCE: 28
cttagccagg gtgcccgtta gaaccacctg gagcaggtca gccccagag gcccgggcag      60 ggcacagctc ccaacagctc agctctccct ggtccaggac nccctgacc gtgtctctcg    120 cctctggcat ggctttgctc tgcccccgct cccagctcct gtctgtcact aacccttcac    180
tctccacctg gggccaggcg g                                                201
```

```
<210> SEQ ID NO 29
<211> LENGTH: 201
<212> TYPE: DNA
<213> ORGANISM: Homo sapiens
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: variation
<222> LOCATION: (101)
<223> OTHER INFORMATION: n=C or T, polymorphic site

<400> SEQUENCE: 29
ataaacccaa tcaagcagaa ggatgggaaa aaataaagag cagaaatcaa taaaactgaa      60
aatagaaaaa tanagaaaac tattgcagga aaaaaaacta naaatgata aacctctatc     120 taacaaaatt gacaactata agaagacacc aaccatcaat atgtggaata aaataggga     180 tgatgtcaca atagattttg c                                              201

<210> SEQ ID NO 30
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or G, polymorphic site

<400> SEQUENCE: 30
ggccaagccc gctcatgatc aaacgctcta agaagaacag cctggccttg tccctgacgg      60
ccgaccagat ggtcagtgcc ttgttggatg ctgagccccc natactctat tccgagtatg    120
atcctaccag acccttcagt gaagcttcga tgatgggctt actgaccaac ctggcagaca    180
gggagctggt tcacatgatc a                                              201

<210> SEQ ID NO 31
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site

<400> SEQUENCE: 31
cgccggctct ccgcgcgcgg gaagtcgagc ccaggacgcc gccttcaggc cggcgcgctg      60
acccggtgcc ccgacccgga gcctgcggtc tgcctggatc ngtcctaaac ctcgcgggct    120
ggacccgcgg cctgagtggg tgggtgtgtg ccagaggatt cgggactagg cccagctccg    180
ggaacctgga aatgtggccc g                                              201

<210> SEQ ID NO 32
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site

<400> SEQUENCE: 32
ccgcaggccc ctgaggagcg atgacggaat ataagctggt ggtggtgggc gccggcggtg      60
tgggcaagag tgcgctgacc atccagctga tccagaacca ntttgtggac gaatacgacc    120
```

```
ccactataga ggtgagcctg gcgccgccgt ccaggtgcca gcagctgctg cgggcgagcc        180
caggacacag ccaggatagg g                                                  201

<210> SEQ ID NO 33
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site
<220> FEATURE:
<221> NAME/KEY: misc_feature
<222> LOCATION: (181)
<223> OTHER INFORMATION: n is a, c, g, or t

<400> SEQUENCE: 33
gtttctggtg acccttttc aggtcttctt ctgttcgttt caaggcattg agctctgcct         60
gggcacgatc catttcctcc ttcatccgcc atctcagttt ntcactgacc gcagagatga      120
gagaggctcg gatggtgtcc tcgctgattg tgccatccct actgggacct gcaggaaaca      180
naggcaaaaa acacttgctt a                                                 201

<210> SEQ ID NO 34
<211> LENGTH: 201
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: variation
<222> LOCATION: (101)
<223> OTHER INFORMATION: n=C or T, polymorphic site

<400> SEQUENCE: 34
agagcatctc cttggacctt tcacagntaa gttactcaaa tgcttcaatt tcaaatattt       60
caaaatttag atttctattt ggtatatccc catgttaatt nactttatat gctgtagaat      120
aatactaaat ttcaacttaa gatggatttt atgccttttt tgctaaatga aagttgggc       180 ttactaaggt ttcatggatc t                                                 201

<210> SEQ ID NO 35
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=A or G, polymorphic site
<220> FEATURE:
<221> NAME/KEY: misc_feature
<222> LOCATION: (120)..(120)
<223> OTHER INFORMATION: n is a, c, g, or t

<400> SEQUENCE: 35
ctgatggagc agatggccac cctggaggct cagccttgct aaatcagaca tttaaatccc       60
gtaatccttg gtgagaggct gccgaggggg aagcagccca ntcctagaag caggggaggn     120 agagaaccttt gtgccagccg tggcggagg ggaggaggga cggttggttc ctgagttatg     180
aatggagcca cccctccct t                                                  201

<210> SEQ ID NO 36
<211> LENGTH: 201
```

```
<212> TYPE: DNA
<213> ORGANISM: Homo sapiens
<220> FEATURE:
<221> NAME/KEY: variation
<222> LOCATION: (101)
<223> OTHER INFORMATION: n=C or T, polymorphic site

<400> SEQUENCE: 36
ttagcctcca attcacagat acctggatgg agcttatctt tcttactagg agggattatc      60
agtggaaatc tgtggtgtat gttggaataa atatcgaata naaattttga tcgaaattat     120
tcagaagcgg ccgggcgcgg tgcctcacgc cttgtaatcc cttcactttg ggagatcaag     180
gcggggggaa tcacctgagg t                                               201

<210> SEQ ID NO 37
<211> LENGTH: 201
<212> TYPE: DNA
<213> ORGANISM: Homo sapiens
<220> FEATURE:
<221> NAME/KEY: variation
<222> LOCATION: (101)
<223> OTHER INFORMATION: n=C or G, polymorphic site

<400> SEQUENCE: 37
agctgggact acaggcgcca ggaggaattc ttatttgagc ttttagttaa ggaaaacagt      60
acagcttgaa agaggaactg ctcaaaagaa tgagtcagtc nctactcacg ctggggagac     120
cctcttgatg agagttttac aggattactc acgaacggcc caggcagggg ccttactagt     180
aagcacgttt tgggaagtcc t                                               201

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
acgttggatg tatcgacacg gagatcctgc                                       30

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
acgttggatg aggaacttga ggtgggtgat                                       30

<210> SEQ ID NO 40
<211> LENGTH: 17
<212> TYPE: DNA
<213> ORGANISM: Artificial Sequence
<220> FEATURE:
<223> OTHER INFORMATION: primer

<400> SEQUENCE: 40
aaccgcaagg acaagtt                                                     17

<210> SEQ ID NO 41
<211> LENGTH: 30
<212> TYPE: DNA
<213> ORGANISM: Artificial Sequence
<220> FEATURE:
```

```
<223> OTHER INFORMATION: primer

<400> SEQUENCE: 41
acgttggatg tgggcaggaa taaggcaaac                                    30

<210> SEQ ID NO 42
<211> LENGTH: 30
<212> TYPE: DNA
<213> ORGANISM: Artificial Sequence
<220> FEATURE:
<223> OTHER INFORMATION: primer

<400> SEQUENCE: 42
acgttggatg ccaataggtt gcctttcctg                                    30

<210> SEQ ID NO 43
<211> LENGTH: 18
<212> TYPE: DNA
<213> ORGANISM: Artificial Sequence
<220> FEATURE:
<223> OTHER INFORMATION: primer

<400> SEQUENCE: 43
caaacaaaca cttcatgc                                                 18

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44
acgttggatg agatctacaa ggctcactgg                                    30

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
acgttggatg tcctttggga agttcctgtc                                    30

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
tggaggtgct taactaacac                                               20

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
acgttggatg ttctgagatg atcctgatgg                                    30
```

```
<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
acgttggatg taaagtatca gatgaagagg                              30

<210> SEQ ID NO 49
<211> LENGTH: 22
<212> TYPE: DNA
<213> ORGANISM: Artificial Sequence
<220> FEATURE:
<223> OTHER INFORMATION: primer

<400> SEQUENCE: 49
atggttttct ttcttgtcct tc                                      22

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
acgttggatg tcttgaagtc tgcaagcacc                              30

<210> SEQ ID NO 51
<211> LENGTH: 31
<212> TYPE: DNA
<213> ORGANISM: Artificial Sequence
<220> FEATURE:
<223> OTHER INFORMATION: primer

<400> SEQUENCE: 51
acgttggatg gcaactttgc tgaattgact g                            31

<210> SEQ ID NO 52
<211> LENGTH: 17
<212> TYPE: DNA
<213> ORGANISM: Artificial Sequence
<220> FEATURE:
<223> OTHER INFORMATION: primer

<400> SEQUENCE: 52
aagcaccaga gtgcttc                                            17

<210> SEQ ID NO 53
<211> LENGTH: 30
<212> TYPE: DNA
<213> ORGANISM: Artificial Sequence
<220> FEATURE:
<223> OTHER INFORMATION: primer

<400> SEQUENCE: 53
acgttggatg gcaagagtct cagaagcatc                              30

<210> SEQ ID NO 54
<211> LENGTH: 30
<212> TYPE: DNA
<213> ORGANISM: Artificial Sequence
<220> FEATURE:
<223> OTHER INFORMATION: primer
```

<400> SEQUENCE: 54
acgttggatg ccctacttgt tctcgttgtc				30

<210> SEQ ID NO 55
<211> LENGTH: 21
<212> TYPE: DNA
<213> ORGANISM: Artificial Sequence
<220> FEATURE:
<223> OTHER INFORMATION: primer

<400> SEQUENCE: 55
atctttctca ggaatgcaat c				21

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
acgttggatg acccactctc tgatttcctg				30

<210> SEQ ID NO 57
<211> LENGTH: 30
<212> TYPE: DNA
<213> ORGANISM: Artificial Sequence
<220> FEATURE:
<223> OTHER INFORMATION: primer

<400> SEQUENCE: 57
acgttggatg aagtctcaga aagtgcccag				30

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
gcatgtcagg ctgcctggaa				20

<210> SEQ ID NO 59
<211> LENGTH: 30
<212> TYPE: DNA
<213> ORGANISM: Artificial Sequence
<220> FEATURE:
<223> OTHER INFORMATION: primer

<400> SEQUENCE: 59
acgttggatg cagtgcactg ataactattc				30

<210> SEQ ID NO 60
<211> LENGTH: 30
<212> TYPE: DNA
<213> ORGANISM: Artificial Sequence
<220> FEATURE:
<223> OTHER INFORMATION: primer

<400> SEQUENCE: 60
acgttggatg gggtttagga aaacaaacct				30

<210> SEQ ID NO 61
<211> LENGTH: 24

```
<212> TYPE: DNA
<213> ORGANISM: Artificial Sequence
<220> FEATURE:
<223> OTHER INFORMATION: primer

<400> SEQUENCE: 61
catgttttca aaaactaagt tact                                          24

<210> SEQ ID NO 62
<211> LENGTH: 30
<212> TYPE: DNA
<213> ORGANISM: Artificial Sequence
<220> FEATURE:
<223> OTHER INFORMATION: primer

<400> SEQUENCE: 62
acgttggatg gataaagtcc tctctgtgcg                                    30

<210> SEQ ID NO 63
<211> LENGTH: 30
<212> TYPE: DNA
<213> ORGANISM: Artificial Sequence
<220> FEATURE:
<223> OTHER INFORMATION: primer

<400> SEQUENCE: 63
acgttggatg gtttcaccac tgtgagcttg                                    30

<210> SEQ ID NO 64
<211> LENGTH: 24
<212> TYPE: DNA
<213> ORGANISM: Artificial Sequence
<220> FEATURE:
<223> OTHER INFORMATION: primer

<400> SEQUENCE: 64
agggtttatt attcagttca caga                                          24

<210> SEQ ID NO 65
<211> LENGTH: 30
<212> TYPE: DNA
<213> ORGANISM: Artificial Sequence
<220> FEATURE:
<223> OTHER INFORMATION: primer

<400> SEQUENCE: 65
acgttggatg gtcactggca caagaacaag                                    30

<210> SEQ ID NO 66
<211> LENGTH: 30
<212> TYPE: DNA
<213> ORGANISM: Artificial Sequence
<220> FEATURE:
<223> OTHER INFORMATION: primer

<400> SEQUENCE: 66
acgttggatg cccatgacat acacgatgag                                    30

<210> SEQ ID NO 67
<211> LENGTH: 17
<212> TYPE: DNA
<213> ORGANISM: Artificial Sequence
<220> FEATURE:
<223> OTHER INFORMATION: primer

<400> SEQUENCE: 67
```
acaagaacaa ggctggc                                      17

<210> SEQ ID NO 68
<211> LENGTH: 30
<212> TYPE: DNA
<213> ORGANISM: Artificial Sequence
<220> FEATURE:
<223> OTHER INFORMATION: primer

<400> SEQUENCE: 68
acgttggatg ccaattagcc caaagcaatg                        30

<210> SEQ ID NO 69
<211> LENGTH: 30
<212> TYPE: DNA
<213> ORGANISM: Artificial Sequence
<220> FEATURE:
<223> OTHER INFORMATION: primer

<400> SEQUENCE: 69
acgttggatg agtagaaggg tgtgtaaggg                        30

<210> SEQ ID NO 70
<211> LENGTH: 21
<212> TYPE: DNA
<213> ORGANISM: Artificial Sequence
<220> FEATURE:
<223> OTHER INFORMATION: primer

<400> SEQUENCE: 70
cccaaagcaa tgaaaaagca a                                 21

<210> SEQ ID NO 71
<211> LENGTH: 30
<212> TYPE: DNA
<213> ORGANISM: Artificial Sequence
<220> FEATURE:
<223> OTHER INFORMATION: primer

<400> SEQUENCE: 71
acgttggatg accttcgtgg tcttcaaacc                        30

<210> SEQ ID NO 72
<211> LENGTH: 30
<212> TYPE: DNA
<213> ORGANISM: Artificial Sequence
<220> FEATURE:
<223> OTHER INFORMATION: primer

<400> SEQUENCE: 72
acgttggatg tacagtccct gagattctgc                        30

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
tcaaaccgca ccccaagctc                                   20

<210> SEQ ID NO 74
<211> LENGTH: 30
<212> TYPE: DNA
<213> ORGANISM: Artificial Sequence

```
<220> FEATURE:
<223> OTHER INFORMATION: primer

<400> SEQUENCE: 74
acgttggatg aaggaaaatt ggggttctgc                                    30

<210> SEQ ID NO 75
<211> LENGTH: 31
<212> TYPE: DNA
<213> ORGANISM: Artificial Sequence
<220> FEATURE:
<223> OTHER INFORMATION: primer

<400> SEQUENCE: 75
acgttggatg ggtgtaagtt tttaagtggc c                                  31

<210> SEQ ID NO 76
<211> LENGTH: 22
<212> TYPE: DNA
<213> ORGANISM: Artificial Sequence
<220> FEATURE:
<223> OTHER INFORMATION: primer

<400> SEQUENCE: 76
gttctgcaat tattaaaaag gg                                            22

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
acgttggatg ctgagctaca gaagcctaag                                    30

<210> SEQ ID NO 78
<211> LENGTH: 29
<212> TYPE: DNA
<213> ORGANISM: Artificial Sequence
<220> FEATURE:
<223> OTHER INFORMATION: primer

<400> SEQUENCE: 78
acgttggatg ctatgcctcg cctggcagc                                     29

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
tgcctttgtg tgctgttccc                                               20

<210> SEQ ID NO 80
<211> LENGTH: 30
<212> TYPE: DNA
<213> ORGANISM: Artificial Sequence
<220> FEATURE:
<223> OTHER INFORMATION: primer

<400> SEQUENCE: 80
acgttggatg aaaaagttcc cggagcagac                                    30
```

```
<210> SEQ ID NO 81
<211> LENGTH: 30
<212> TYPE: DNA
<213> ORGANISM: Artificial Sequence
<220> FEATURE:
<223> OTHER INFORMATION: primer

<400> SEQUENCE: 81
acgttggatg ctgagggtta ctcgctgctg                                              30

<210> SEQ ID NO 82
<211> LENGTH: 19
<212> TYPE: DNA
<213> ORGANISM: Artificial Sequence
<220> FEATURE:
<223> OTHER INFORMATION: primer

<400> SEQUENCE: 82
ggaaatggga ggtaccggc                                                          19

<210> SEQ ID NO 83
<211> LENGTH: 30
<212> TYPE: DNA
<213> ORGANISM: Artificial Sequence
<220> FEATURE:
<223> OTHER INFORMATION: primer

<400> SEQUENCE: 83
acgttggatg ccatgtgcct tcatgaacag                                              30

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84
acgttggatg agactcagct tcagagatgg                                              30

<210> SEQ ID NO 85
<211> LENGTH: 18
<212> TYPE: DNA
<213> ORGANISM: Artificial Sequence
<220> FEATURE:
<223> OTHER INFORMATION: primer

<400> SEQUENCE: 85
aatggcaatg tcagtagc                                                           18

<210> SEQ ID NO 86
<211> LENGTH: 30
<212> TYPE: DNA
<213> ORGANISM: Artificial Sequence
<220> FEATURE:
<223> OTHER INFORMATION: primer

<400> SEQUENCE: 86
acgttggatg atcatgaaga aggagcccac                                              30

<210> SEQ ID NO 87
<211> LENGTH: 30
<212> TYPE: DNA
<213> ORGANISM: Artificial Sequence
<220> FEATURE:
<223> OTHER INFORMATION: primer
```

<400> SEQUENCE: 87
acgttggatg atgtggtggc tggcattgtg                                    30

<210> SEQ ID NO 88
<211> LENGTH: 19
<212> TYPE: DNA
<213> ORGANISM: Artificial Sequence
<220> FEATURE:
<223> OTHER INFORMATION: primer

<400> SEQUENCE: 88
tggggacagg aagaggaaa                                                19

<210> SEQ ID NO 89
<211> LENGTH: 30
<212> TYPE: DNA
<213> ORGANISM: Artificial Sequence
<220> FEATURE:
<223> OTHER INFORMATION: primer

<400> SEQUENCE: 89
acgttggatg tttgtggcag agctctaaag                                    30

<210> SEQ ID NO 90
<211> LENGTH: 30
<212> TYPE: DNA
<213> ORGANISM: Artificial Sequence
<220> FEATURE:
<223> OTHER INFORMATION: primer

<400> SEQUENCE: 90
acgttggatg aggcatcctc tttgtctttg                                    30

<210> SEQ ID NO 91
<211> LENGTH: 23
<212> TYPE: DNA
<213> ORGANISM: Artificial Sequence
<220> FEATURE:
<223> OTHER INFORMATION: primer

<400> SEQUENCE: 91
ggcagagctc taaagaaatg act                                           23

<210> SEQ ID NO 92
<211> LENGTH: 30
<212> TYPE: DNA
<213> ORGANISM: Artificial Sequence
<220> FEATURE:
<223> OTHER INFORMATION: primer

<400> SEQUENCE: 92
acgttggatg aaggctgttc atgagaaggc                                    30

<210> SEQ ID NO 93
<211> LENGTH: 31
<212> TYPE: DNA
<213> ORGANISM: Artificial Sequence
<220> FEATURE:
<223> OTHER INFORMATION: primer

<400> SEQUENCE: 93
acgttggatg cacaacactg aataattaat g                                  31

<210> SEQ ID NO 94

-continued

```
<211> LENGTH: 19
<212> TYPE: DNA
<213> ORGANISM: Artificial Sequence
<220> FEATURE:
<223> OTHER INFORMATION: primer

<400> SEQUENCE: 94
atgagaaggc cttgaaaag                                                    19

<210> SEQ ID NO 95
<211> LENGTH: 29
<212> TYPE: DNA
<213> ORGANISM: Artificial Sequence
<220> FEATURE:
<223> OTHER INFORMATION: primer

<400> SEQUENCE: 95
acgttggatg agcgccctca tcccggtgg                                         29

<210> SEQ ID NO 96
<211> LENGTH: 30
<212> TYPE: DNA
<213> ORGANISM: Artificial Sequence
<220> FEATURE:
<223> OTHER INFORMATION: primer

<400> SEQUENCE: 96
acgttggatg agtctcgagc gcagaatcag                                        30

<210> SEQ ID NO 97
<211> LENGTH: 17
<212> TYPE: DNA
<213> ORGANISM: Artificial Sequence
<220> FEATURE:
<223> OTHER INFORMATION: primer

<400> SEQUENCE: 97
gtggggcggc ccgcatg                                                      17

<210> SEQ ID NO 98
<211> LENGTH: 30
<212> TYPE: DNA
<213> ORGANISM: Artificial Sequence
<220> FEATURE:
<223> OTHER INFORMATION: primer

<400> SEQUENCE: 98
acgttggatg tgacctgcca cccagtacct                                        30

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
acgttggatg aacgcatgga gcccacctat                                        30

<210> SEQ ID NO 100
<211> LENGTH: 17
<212> TYPE: DNA
<213> ORGANISM: Artificial Sequence
<220> FEATURE:
<223> OTHER INFORMATION: primer

<400> SEQUENCE: 100
```
cccagtacct ccattac                                               17

<210> SEQ ID NO 101
<211> LENGTH: 30
<212> TYPE: DNA
<213> ORGANISM: Artificial Sequence
<220> FEATURE:
<223> OTHER INFORMATION: primer

<400> SEQUENCE: 101
acgttggatg tgcccattaa cattctggag                                 30

<210> SEQ ID NO 102
<211> LENGTH: 30
<212> TYPE: DNA
<213> ORGANISM: Artificial Sequence
<220> FEATURE:
<223> OTHER INFORMATION: primer

<400> SEQUENCE: 102
acgttggatg atctgctttc tgtccctatg                                 30

<210> SEQ ID NO 103
<211> LENGTH: 21
<212> TYPE: DNA
<213> ORGANISM: Artificial Sequence
<220> FEATURE:
<223> OTHER INFORMATION: primer

<400> SEQUENCE: 103
ggagaatatc actgatctgc a                                          21

<210> SEQ ID NO 104
<211> LENGTH: 30
<212> TYPE: DNA
<213> ORGANISM: Artificial Sequence
<220> FEATURE:
<223> OTHER INFORMATION: primer

<400> SEQUENCE: 104
acgttggatg ccttagaaag acacttgtac                                 30

<210> SEQ ID NO 105
<211> LENGTH: 30
<212> TYPE: DNA
<213> ORGANISM: Artificial Sequence
<220> FEATURE:
<223> OTHER INFORMATION: primer

<400> SEQUENCE: 105
acgttggatg attcccttcc ttcgaaatgc                                 30

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
cacttgtact tacatgtcaa                                            20

<210> SEQ ID NO 107
<211> LENGTH: 30
<212> TYPE: DNA

<213> ORGANISM: Artificial Sequence
<220> FEATURE:
<223> OTHER INFORMATION: primer

<400> SEQUENCE: 107
acgttggatg accatgaccc tccacaccaa                30

<210> SEQ ID NO 108
<211> LENGTH: 30
<212> TYPE: DNA
<213> ORGANISM: Artificial Sequence
<220> FEATURE:
<223> OTHER INFORMATION: primer

<400> SEQUENCE: 108
acgttggatg tcgttccctt ggatctgatg                30

<210> SEQ ID NO 109
<211> LENGTH: 17
<212> TYPE: DNA
<213> ORGANISM: Artificial Sequence
<220> FEATURE:
<223> OTHER INFORMATION: primer

<400> SEQUENCE: 109
ctccacacca aagcatc                17

<210> SEQ ID NO 110
<211> LENGTH: 30
<212> TYPE: DNA
<213> ORGANISM: Artificial Sequence
<220> FEATURE:
<223> OTHER INFORMATION: primer

<400> SEQUENCE: 110
acgttggatg agacttctac agttcagtcg                30

<210> SEQ ID NO 111
<211> LENGTH: 30
<212> TYPE: DNA
<213> ORGANISM: Artificial Sequence
<220> FEATURE:
<223> OTHER INFORMATION: primer

<400> SEQUENCE: 111
acgttggatg ccatcaatgc aagttcttcc                30

<210> SEQ ID NO 112
<211> LENGTH: 23
<212> TYPE: DNA
<213> ORGANISM: Artificial Sequence
<220> FEATURE:
<223> OTHER INFORMATION: primer

<400> SEQUENCE: 112
tgtgggattg atatcatcta gtc                23

<210> SEQ ID NO 113
<211> LENGTH: 30
<212> TYPE: DNA
<213> ORGANISM: Artificial Sequence
<220> FEATURE:
<223> OTHER INFORMATION: primer

<400> SEQUENCE: 113
acgttggatg ttatctgaac cgtgtgggag                30

<210> SEQ ID NO 114
<211> LENGTH: 30
<212> TYPE: DNA
<213> ORGANISM: Artificial Sequence
<220> FEATURE:
<223> OTHER INFORMATION: primer

<400> SEQUENCE: 114
acgttggatg catcgcattc cttgcaaaag                           30

<210> SEQ ID NO 115
<211> LENGTH: 18
<212> TYPE: DNA
<213> ORGANISM: Artificial Sequence
<220> FEATURE:
<223> OTHER INFORMATION: primer

<400> SEQUENCE: 115
gccagggagc tctcagac                                        18

<210> SEQ ID NO 116
<211> LENGTH: 30
<212> TYPE: DNA
<213> ORGANISM: Artificial Sequence
<220> FEATURE:
<223> OTHER INFORMATION: primer

<400> SEQUENCE: 116
acgttggatg gcaagcaaga agcagacatc                           30

<210> SEQ ID NO 117
<211> LENGTH: 30
<212> TYPE: DNA
<213> ORGANISM: Artificial Sequence
<220> FEATURE:
<223> OTHER INFORMATION: primer

<400> SEQUENCE: 117
acgttggatg aatctaccaa gagccatgcc                           30

<210> SEQ ID NO 118
<211> LENGTH: 17
<212> TYPE: DNA
<213> ORGANISM: Artificial Sequence
<220> FEATURE:
<223> OTHER INFORMATION: primer

<400> SEQUENCE: 118
atctactcct tttcccc                                         17

<210> SEQ ID NO 119
<211> LENGTH: 30
<212> TYPE: DNA
<213> ORGANISM: Artificial Sequence
<220> FEATURE:
<223> OTHER INFORMATION: primer

<400> SEQUENCE: 119
acgttggatg agagcaaagc catgccagag                           30

<210> SEQ ID NO 120
<211> LENGTH: 30
<212> TYPE: DNA
<213> ORGANISM: Artificial Sequence
<220> FEATURE:

```
<223> OTHER INFORMATION: primer

<400> SEQUENCE: 120
acgttggatg cacagctccc aacagctcag                                          30

<210> SEQ ID NO 121
<211> LENGTH: 18
<212> TYPE: DNA
<213> ORGANISM: Artificial Sequence
<220> FEATURE:
<223> OTHER INFORMATION: primer

<400> SEQUENCE: 121
gagagacacg gtcagggg                                                       18

<210> SEQ ID NO 122
<211> LENGTH: 30
<212> TYPE: DNA
<213> ORGANISM: Artificial Sequence
<220> FEATURE:
<223> OTHER INFORMATION: primer

<400> SEQUENCE: 122
acgttggatg gaaaactatt gcaggaaaaa                                          30

<210> SEQ ID NO 123
<211> LENGTH: 30
<212> TYPE: DNA
<213> ORGANISM: Artificial Sequence
<220> FEATURE:
<223> OTHER INFORMATION: primer

<400> SEQUENCE: 123
acgttggatg ccacatattg atggttggtg                                          30

<210> SEQ ID NO 124
<211> LENGTH: 22
<212> TYPE: DNA
<213> ORGANISM: Artificial Sequence
<220> FEATURE:
<223> OTHER INFORMATION: primer

<400> SEQUENCE: 124
actattgcag gaaaaaaaac ta                                                  22

<210> SEQ ID NO 125
<211> LENGTH: 30
<212> TYPE: DNA
<213> ORGANISM: Artificial Sequence
<220> FEATURE:
<223> OTHER INFORMATION: primer

<400> SEQUENCE: 125
acgttggatg agatggtcag tgccttgttg                                          30

<210> SEQ ID NO 126
<211> LENGTH: 30
<212> TYPE: DNA
<213> ORGANISM: Artificial Sequence
<220> FEATURE:
<223> OTHER INFORMATION: primer

<400> SEQUENCE: 126
acgttggatg aagcttcact gaagggtctg                                          30
```

```
<210> SEQ ID NO 127
<211> LENGTH: 17
<212> TYPE: DNA
<213> ORGANISM: Artificial Sequence
<220> FEATURE:
<223> OTHER INFORMATION: primer

<400> SEQUENCE: 127
ttggatgctg agccccc                                                    17

<210> SEQ ID NO 128
<211> LENGTH: 30
<212> TYPE: DNA
<213> ORGANISM: Artificial Sequence
<220> FEATURE:
<223> OTHER INFORMATION: primer

<400> SEQUENCE: 128
acgttggatg aatcctctgg cacacaccca                                       30

<210> SEQ ID NO 129
<211> LENGTH: 29
<212> TYPE: DNA
<213> ORGANISM: Artificial Sequence
<220> FEATURE:
<223> OTHER INFORMATION: primer

<400> SEQUENCE: 129
acgttggatg gacccggagc ctgcggtct                                        29

<210> SEQ ID NO 130
<211> LENGTH: 17
<212> TYPE: DNA
<213> ORGANISM: Artificial Sequence
<220> FEATURE:
<223> OTHER INFORMATION: primer

<400> SEQUENCE: 130
cccgcgaggt ttaggac                                                    17

<210> SEQ ID NO 131
<211> LENGTH: 30
<212> TYPE: DNA
<213> ORGANISM: Artificial Sequence
<220> FEATURE:
<223> OTHER INFORMATION: primer

<400> SEQUENCE: 131
acgttggatg atagtggggt cgtattcgtc                                       30

<210> SEQ ID NO 132
<211> LENGTH: 30
<212> TYPE: DNA
<213> ORGANISM: Artificial Sequence
<220> FEATURE:
<223> OTHER INFORMATION: primer

<400> SEQUENCE: 132
acgttggatg atataagctg gtggtggtgg                                       30

<210> SEQ ID NO 133
<211> LENGTH: 17
<212> TYPE: DNA
<213> ORGANISM: Artificial Sequence
<220> FEATURE:
<223> OTHER INFORMATION: primer
```

```
<400> SEQUENCE: 133
tcgtattcgt ccacaaa                                                  17

<210> SEQ ID NO 134
<211> LENGTH: 30
<212> TYPE: DNA
<213> ORGANISM: Artificial Sequence
<220> FEATURE:
<223> OTHER INFORMATION: primer

<400> SEQUENCE: 134
acgttggatg tccatttcct ccttcatccg                                    30

<210> SEQ ID NO 135
<211> LENGTH: 30
<212> TYPE: DNA
<213> ORGANISM: Artificial Sequence
<220> FEATURE:
<223> OTHER INFORMATION: primer

<400> SEQUENCE: 135
acgttggatg agtagggatg gcacaatcag                                    30

<210> SEQ ID NO 136
<211> LENGTH: 21
<212> TYPE: DNA
<213> ORGANISM: Artificial Sequence
<220> FEATURE:
<223> OTHER INFORMATION: primer

<400> SEQUENCE: 136
cttcatccgc catctcagtt t                                             21

<210> SEQ ID NO 137
<211> LENGTH: 30
<212> TYPE: DNA
<213> ORGANISM: Artificial Sequence
<220> FEATURE:
<223> OTHER INFORMATION: primer

<400> SEQUENCE: 137
acgttggatg ctatttggta tatccccatg                                    30

<210> SEQ ID NO 138
<211> LENGTH: 30
<212> TYPE: DNA
<213> ORGANISM: Artificial Sequence
<220> FEATURE:
<223> OTHER INFORMATION: primer

<400> SEQUENCE: 138
acgttggatg gcaaaaaagg cataaaatcc                                    30

<210> SEQ ID NO 139
<211> LENGTH: 24
<212> TYPE: DNA
<213> ORGANISM: Artificial Sequence
<220> FEATURE:
<223> OTHER INFORMATION: primer

<400> SEQUENCE: 139
atttggtata tccccatgtt aatt                                          24

<210> SEQ ID NO 140
<211> LENGTH: 30
```

```
<210> SEQ ID NO 140
<211> LENGTH: 30
<212> TYPE: DNA
<213> ORGANISM: Artificial Sequence
<220> FEATURE:
<223> OTHER INFORMATION: primer

<400> SEQUENCE: 140
acgttggatg acggctggca caaggttctc                                           30

<210> SEQ ID NO 141
<211> LENGTH: 30
<212> TYPE: DNA
<213> ORGANISM: Artificial Sequence
<220> FEATURE:
<223> OTHER INFORMATION: primer

<400> SEQUENCE: 141
acgttggatg taatccttgg tgagaggctg                                           30

<210> SEQ ID NO 142
<211> LENGTH: 18
<212> TYPE: DNA
<213> ORGANISM: Artificial Sequence
<220> FEATURE:
<223> OTHER INFORMATION: primer

<400> SEQUENCE: 142
cctcccctgc ttctagga                                                        18

<210> SEQ ID NO 143
<211> LENGTH: 30
<212> TYPE: DNA
<213> ORGANISM: Artificial Sequence
<220> FEATURE:
<223> OTHER INFORMATION: primer

<400> SEQUENCE: 143
acgttggatg ctaggaggga ttatcagtgg                                           30

<210> SEQ ID NO 144
<211> LENGTH: 30
<212> TYPE: DNA
<213> ORGANISM: Artificial Sequence
<220> FEATURE:
<223> OTHER INFORMATION: primer

<400> SEQUENCE: 144
acgttggatg gccgcttctg aataatttcg                                           30

<210> SEQ ID NO 145
<211> LENGTH: 24
<212> TYPE: DNA
<213> ORGANISM: Artificial Sequence
<220> FEATURE:
<223> OTHER INFORMATION: primer

<400> SEQUENCE: 145
gtatgttgga ataaatatcg aata                                                 24

<210> SEQ ID NO 146
<211> LENGTH: 30
<212> TYPE: DNA
<213> ORGANISM: Artificial Sequence
<220> FEATURE:
<223> OTHER INFORMATION: primer

<400> SEQUENCE: 146
```

```
acgttggatg actctcatca agagggtctc                                      30

<210> SEQ ID NO 147
<211> LENGTH: 30
<212> TYPE: DNA
<213> ORGANISM: Artificial Sequence
<220> FEATURE:
<223> OTHER INFORMATION: primer

<400> SEQUENCE: 147
acgttggatg cagcttgaaa gaggaactgc                                      30

<210> SEQ ID NO 148
<211> LENGTH: 20
<212> TYPE: DNA
<213> ORGANISM: Artificial Sequence
<220> FEATURE:
<223> OTHER INFORMATION: primer

<400> SEQUENCE: 148
ggtctcccca gcgtgagtag                                                 20
```